United States Patent
Hayward

(10) Patent No.: US 6,974,817 B2
(45) Date of Patent: Dec. 13, 2005

(54) SULFONIC ACID DERIVATIVES

(75) Inventor: Matthew M. Hayward, Old Lyme, CT (US)

(73) Assignee: Pfizer Inc., New York, NY (US)

( * ) Notice: Subject to any disclaimer, the term of this patent is extended or adjusted under 35 U.S.C. 154(b) by 118 days.

(21) Appl. No.: 10/175,645

(22) Filed: Jun. 19, 2002

(65) Prior Publication Data

US 2003/0083335 A1 May 1, 2003

Related U.S. Application Data

(60) Provisional application No. 60/299,461, filed on Jun. 20, 2001.

(51) Int. Cl.[7] .................... A66K 31/495; C07D 241/04
(52) U.S. Cl. .................... 514/253.01; 514/253.12; 514/255.01; 544/360; 544/391
(58) Field of Search ................ 544/360, 391; 514/253.01, 255.01, 253.12

(56) References Cited

U.S. PATENT DOCUMENTS

| | | | |
|---|---|---|---|
| 3,119,742 A | 1/1964 | Heimlich et al. | 167/82 |
| 3,492,397 A | 1/1970 | Peters et al. | 424/20 |
| 3,538,214 A | 11/1970 | Polli et al. | 424/19 |
| 4,060,598 A | 11/1977 | Groppenbacher et al. | 424/33 |
| 4,173,626 A | 11/1979 | Dempski et al. | 424/19 |
| 2002/0107255 A1 | 8/2002 | Blumberg et al. | |
| 2002/0119961 A1 | 8/2002 | Blumberg et al. | |

FOREIGN PATENT DOCUMENTS

| WO | WO9856771 | 12/1998 |
|---|---|---|
| WO | WO0172728 | 10/2001 |

OTHER PUBLICATIONS

Combadiere, Christophe, et. al., "Monocyte Chemoattractant Protein–3 is a Functional Ligand for CC Chemokine Receptors 1 and 2B," The Journal of Biological Chemistry, vol. 270, No. 50, 1995, pp. 29671–29675.

Teran, Luis M., et. al., "Eosinophil Recruitment Following Allergen Challenge is Associated with the Release of the Chemokine RANTES into Asthmatic Airways," The Journal of Immunology, 157, 1996, pp. 1806–1812.

Smith, Robert E., et. al., "Production and Function of Murine Macrophage Inflammatory Protein–1α in Bleomycin–Induced Lung Injury," The Journal of Immunology, 153, 1994, pp. 4704–4712.

Cook, Donald N., et. al., "Requirement of MIP–1α for an Inflammatory Response to Viral Infection," Science, vol. 269, 1995, pp. 583–585.

Maryanoff, Bruce E., et. al., "Stereochemistry of the Wittig Reaction. Effect of Nucleophilic Groups in the Phosphonium Ylide," J. Am. Chem. Soc. 107, 1985, pp. 217–226.

Coligan, J.E., et. al., "Chapter 6: Cytokines and Their Cellular Receptors, Unit 6.12 Biological Responses to Chemokine Superfamily Members," Current Protocols in Immunology, 1991, pp. 1–5.

Elworthy, Todd, R. et. al., *N*–Arylpiperazinyl–*N*'–propylamino Derivatives of Heteroaryl Amides as Functional Uroselective α1–Adrenoceptor Antagonists, J. Med. Chem, 40, 1997, pp. 2674–2687.

Liang, M., et al., *Identification and Characterization of a Potent, Selective, and Orally Active Agonist of the CC Chemokine Receptor–1, Journal of Biological Chemistry*, vol. 275, No. 25, pp. 19000–19008, (Jun. 23, 2000).

*Primary Examiner*—Richard L. Raymond
(74) *Attorney, Agent, or Firm*—Gregg C. Benson; Christopher J. Verni

(57) ABSTRACT

A compound of the formula

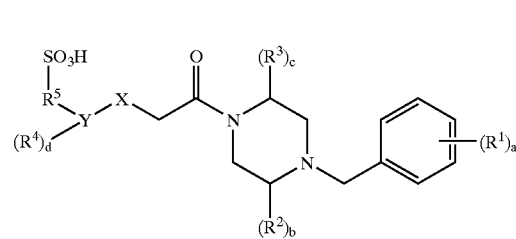

or the pharmaceutically acceptable salt thereof; wherein X, Y, a, b, c, d, $R^1$, $R^2$, $R^3$ and $R^5$ are as defined above useful to treat inflammation and other immune disorders.

53 Claims, No Drawings

SULFONIC ACID DERIVATIVES

CROSS-REFERENCE TO RELATED APPLICATION

This non-provisional application claims priority of U.S. provisional application No. 60/299,461, filed Jun. 20, 2001.

BACKGROUND OF THE INVENTION

The present invention relates to novel sulfonic acid derivatives, methods of use and pharmaceutical compositions containing them.

The compounds of the invention are potent and selective inhibitors of MIP-1α (CCL3) binding to its receptor CCR1 found on inflammatory and immunomodulatory cells (preferably leukocytes and lymphocytes). The CCR1 receptor is also sometimes referred to as the CC-CKR1 receptor. These compounds also inhibit MIP-1α (and the related chemokines shown to interact with CCR1 (e.g., RANTES (CCL5), MCP-2 (CCL8), MCP-3 (CCL7), HCC-1 (CCL14) and HCC-2 (CCL15))) induced chemotaxis of THP-1 cells and human leukocytes and are potentially useful for the treatment or prevention of autoimmune diseases (such as rheumatoid arthritis, type I diabetes (recent onset), lupus, inflammatory bowel disease, optic neuritis, psoriasis, multiple sclerosis, polymyalgia rheumatica, uveitis, and vasculitis), acute and chronic inflammatory conditions (such as osteoarthritis, adult Respiratory Distress Syndrome, Respiratory Distress Syndrome of infancy, ischemia reperfusion injury, and glomerulonephritis), allergic conditions (such as asthma and atopic dermatitis), infection associated with inflammation (such as viral inflammation (including influenza and hepatitis) and Guillian-Barre), chronic bronchitis, xeno-transplantation, transplantation tissue rejection (chronic and acute), organ rejection (chronic and acute), atherosclerosis, restenosis (including, but not limited to, restenosis following balloon and/or stent insertion), HIV infectivity (co-receptor usage), and granulomatous diseases (including sarcoidosis, leprosy and tuberculosis) and sequelae associated with certain cancers such as multiple myeloma. Compounds in this series may also have utility for the prevention of cancer metastasis. Compounds in this series may also limit the production of cytokines at inflammatory sites, including but not limited to TNF and IL-1, as a consequence of decreasing cell infiltration, providing benefit for diseases linked to TNF and IL-1, including congestive heart failure, pulmonary emphysema or dyspnea associated therewith, emphysema; HIV-1, HIV-2, HIV-3; cytomegalovirus (CMV), adenoviruses, Herpes viruses (*Herpes zoster* and *Herpes simplex*). They may also provide benefit for the sequelae associated with infection where such infection induces production of detrimental inflammatory cytokines such as TNF e.g, fungal meningitis, joint tissue damage, hyperplasia, pannus formation and bone resorption, psoriatic arthritis, hepatic failure, bacterial meningitis, Kawasaki syndrome, myocardial infarction, acute liver failure, lyme disease, septic shock, cancer, trauma, and malaria, etc.

MIP-1α and RANTES are soluble chemotactic peptides (chemokines) which are produced by inflammatory cells, in particular CD8+ lymphocytes, polymorphonuclear leukocytes (PMNs) and macrophages, *J. Biol. Chem.,* 270 (30) 29671–29675 (1995). These chemokines act by inducing the migration and activation of key inflammatory and immunomodulatory cells. Elevated levels of chemokines have been found in the synovial fluid of rheumatoid arthritis patients, chronic and rejecting tissue from transplant patients and in the nasal secretions of allergic rhinitis patients following allergen exposure (Teran, et al., *J. Immunol.,* 1806–1812 (1996), and Kuna et al., *J. Allergy Clin. Immunol.* 321 (1994)). Antibodies which interfere with the chemokine/receptor interaction by neutralizing MIP1α or gene disruption have provided direct evidence for the role of MIP-1α and RANTES in disease by limiting the recruitment of monocytes and CD8+ lymphocytes (Smith et al., *J. Immunol,* 153, 4704 (1994) and Cook et al., *Science,* 269, 1583 (1995)). Together this data demonstrates that CCR1 receptor antagonists would be an effective treatment of several immune based diseases. The compounds described within are potent and selective antagonists of the CCR1 receptor.

SUMMARY OF THE INVENTION

A compound of the formula

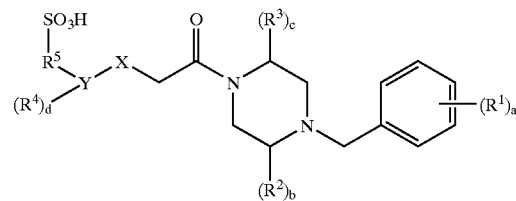

or the pharmaceutically acceptable salts and prodrugs thereof; wherein
a=0–5,
b=0–2,
c=0–2
d=0–4
X is —O—, —S—, —CH$_2$—, —NR$^6$—
Y is (C$_6$–C$_{10}$)aryl, or (C$_2$–C$_9$)heteroaryl,
each R$^1$ is independently selected from the group consisting of: H—, HO—, halo-, (C$_1$–C$_8$)alkyl-optionally substituted with 1–3 fluorine atoms, (C$_1$–C$_8$)alkyl-O— wherein the alkyl group is optionally substituted with 1–3 fluorine atoms, HO—(C$_1$–C$_8$)alkyl-, NC—, H$_2$N—, H$_2$N—(C$_1$–C$_8$)alkyl-, HO—(C=O)—, (C$_1$–C$_8$)alkyl-(C=O)—, (C$_1$–C$_8$)alkyl-(C=O)—(C$_1$–C$_8$)alkyl-, H$_2$N—(C=O)—, H$_2$N—(C=O)—(C$_1$–C$_8$)alkyl-;
each R$^2$ and R$^3$ is independently selected from the group consisting of: H—, oxo, (C$_1$–C$_8$)alkyl-optionally substituted with 1–3 fluorine atoms, (C$_1$–C$_8$)alkyl-, (C$_6$–C$_{10}$)aryl-, (C$_6$–C$_{10}$)aryl-(C$_1$–C$_8$)alkyl-, HO—(C$_1$–C$_8$)alkyl-, (C$_1$–C$_8$)alkyl-O—(C$_1$–C$_8$)alkyl-, H$_2$N—(C$_1$–C$_8$)alkyl-, (C$_1$–C$_8$)alkyl-NH—(C$_1$–C$_8$)alkyl-, [(C$_1$–C$_8$)alkyl]$_2$N—(C$_1$–C$_8$)alkyl-, (C$_2$–C$_9$)heterocyclyl-(C$_1$–C$_8$)alkyl-, (C$_1$–C$_8$)alkyl-(C=O)—NH—(C$_1$–C$_8$)alkyl-, (C$_1$–C$_8$)alkyl-O—(C=O)—NH—(C$_1$–C$_8$)alkyl-, H$_2$N—(C=O)—NH—(C$_1$–C$_8$)alkyl-, (C$_1$–C$_8$)alkyl-SO$_2$—NH—(C$_1$–C$_8$)alkyl-, (C$_2$–C$_9$)heteroaryl-(C$_1$–C$_8$)alkyl-, H$_2$N—(C=O)—, H$_2$N—(C=O)—(C$_1$–C$_8$)alkyl-;
each R$^4$ is independently selected from the group consisting of: H—, HO—, halo-, NC—, HO—(C=O)—, H$_2$N—, (C$_1$–C$_8$)alkyl-NH—, [(C$_1$–C$_8$)alkyl]$_2$N—, (C$_1$–C$_8$)alkyl-optionally substituted with 1–3 fluorine atoms, (C$_1$–C$_8$)alkyl-O— wherein the alkyl group is optionally substituted with 1–3 fluorine atoms, HO—(C$_1$–C$_8$)alkyl-, (C$_1$–C$_8$)alkyl-O—(C$_1$–C$_8$)alkyl-, H$_2$N—(C$_1$–C$_8$)alkyl-, (C$_1$–C$_8$)alkyl-NH—(C$_1$–C$_8$)alkyl-, [(C$_1$–C$_8$)alkyl]$_2$N—(C$_1$–C$_8$)alkyl-, (C$_1$–C$_8$)alkyl-(C=O)—, (C$_1$–C$_8$)alkyl-(C=O)—(C$_1$–C$_8$)alkyl-, (C$_6$–C$_{10}$)aryl-, (C$_2$–C$_9$)

heteroaryl-, $(C_6-C_{10})$aryloxy-, —$SO_2NH_2$, —$NHSO_2$—$(C_1-C_8)$alkyl-, $H_2N$—(C=O)—, $H_2N$—(C=O)—$(C_1-C_8)$alkyl-, $(C_1-C_8)$alkyl-NH—(C=O)—, $(C_1-C_8)$alkyl-NH—(C=O)—$(C_1-C_8)$alkyl-, [$(C_1-C_8)$alkyl]$_2$N—(C=O)—, [$(C_1-C_8)$alkyl]$_2$-N—(C=O)—$(C_1-C_8)$alkyl-, $(C_3-C_8)$cycloalkyl-, $(C_1-C_8)$alkyl-$SO_2$—, NC—$(C_1-C_8)$alkyl-, $(C_1-C_8)$alkyl-(C=O)—NH—, $H_2N$—(C=O)—NH—, $H_2N$—(C=O)—NH—$(C_1-C_8)$alkyl-;

$R^5$ is $(C_1-C_8)$alkyl-.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as, but not limited to, the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (i.e., 1,1'-methylene-bis-(2-hydroxy-3-naphthoate)) salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The compounds of this invention may contain olefin-like double bonds. When such bonds are present, the compounds of the invention exist as cis and trans configurations and as mixtures thereof.

The present invention also relates to compounds of formula I wherein any of the hydrogens may optionally be replaced by deuterium.

Unless otherwise indicated, the alkyl groups referred to herein may be linear or branched, and they may also be cyclic (e.g., cyclopropyl, cyclobutyl, cyclopentyl, cyclohexyl, cycloheptyl) or bicyclic (e.g., norbornanyl, bicyclo[3.2.1]octane) or contain cyclic groups. They may also contain zero to two levels of unsaturation and may be optionally substituted with 1 to 3 substituents independently selected from the group consisting of but not limited to: halo-, HO—, NC—, $H_2N$—, HO—(C=O)—.

Unless otherwise indicated, halogen includes fluorine, chlorine, bromine, and iodine.

$(C_2-C_9)$Heterocyclyl- when used herein refers to, but is not limited to, pyrrolidinyl, tetrahydrofuranyl, dihydrofuranyl, tetrahydropyranyl, pyranyl, thiopyranyl, aziridinyl, oxiranyl, methylenedioxyl, chromenyl, barbituryl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl and chromanyl. Said $(C_2-C_9)$heterocyclyl ring is attached through a carbon or a nitrogen atom.

$(C_2-C_9)$Heteroaryl when used herein refers to, but is not limited to, furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydroquinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl and benzoxazinyl. and may be optionally substituted with 1 to 3 substituents independently selected from the group consisting of, but not limited to: H—, HO—, halo-, $(C_1-C_8)$alkyl-optionally substituted with 1–3 fluorine atoms, $(C_1-C_8)$alkyl-O— wherein the alkyl group is optionally substituted with 1–3 fluorine atoms, HO—$(C_1-C_8)$alkyl-, NC—, $H_2N$—, $H_2N$—$(C_1-C_8)$alkyl-, HO—(C=O)—, $(C_1-C_8)$alkyl-(C=O)—, $(C_1-C_8)$alkyl-(C=O)—$(C_1-C_8)$alkyl-, $H_2N$—(C=O)—, $H_2N$—(C=O)—$(C_1-C_8)$alkyl-, $H_2NSO_2$—, $(C_1-C_8)$alkyl-$SO_2$—NH—.

Aryl when used herein refers to phenyl or naphthyl which may be optionally substituted with 1 to 3 substituents independently selected from the group consisting of but not limited to: H—, HO—, halo-, $(C_1-C_8)$alkyl-optionally substituted with 1–3 fluorine atoms, $(C_1-C_8)$alkyl-O— wherein the alkyl group is optionally substituted with 1–3 fluorine atoms, HO—$(C_1-C_8)$alkyl-, NC—, $H_2N$—, $H_2N$—$(C_1-C_8)$alkyl-, HO—(C=O)—, $(C_1-C_8)$alkyl-(C=O)—, $(C_1-C_8)$alkyl-(C=O)—$(C_1-C_8)$alkyl-, $H_2N$—(C=O)—, $H_2N$—(C=O)—$(C_1-C_8)$alkyl-, $H_2NSO_2$—, $(C_1-C_8)$alkyl-$SO_2$—NH—;

The compounds of this invention include all conformational isomers (e.g., cis and trans isomers) and all optical isomers of compounds of the formula I (e.g., enantiomers and diastereomers), as well as racemic, diastereomeric and other mixtures of such isomers.

Examples of specific preferred compounds of the formula I are the following:

(5-Bromo-2-{2-[4-(4-fluoro-benzyl)-2R-methyl-piperazin-1-yl]-2-oxo-ethoxy}-phenyl)-methanesulfonic acid;

(5-Chloro-2-{2-[4-(4-chloro-benzyl)-2R,5S-dimethyl-piperazin-1-yl]-2-oxo-ethoxy}-phenyl)-methanesulfonic acid;

2-(5-Bromo-2-{2-[4-(4-fluoro-benzyl)-2R-methyl-piperazin-1-yl]-2-oxo-ethoxy}-phenyl)-ethanesulfonic acid;

2-(5-Chloro-2-{2-[4-(4-chloro-benzyl)-2R,5S-dimethyl-piperazin-1-yl]-2-oxo-ethoxy}-phenyl)-ethanesulfonic acid;

(4-Bromo-2-{2-[4-(4-fluoro-benzyl)-2R,5S-dimethyl-piperazin-1-yl]-2-oxo-ethoxy}-phenyl)-methanesulfonic acid;

(3-Chloro-2-{2-[4-(4-fluoro-benzyl)-2R,5S-dimethyl-piperazin-1-yl]-2-oxo-ethoxy}-phenyl)-methanesulfonic acid;

(5-Bromo-2-{2-[4-(4-chloro-benzyl)-2R,5S-dimethyl-piperazin-1-yl]-2-oxo-ethoxy}-phenyl)-methanesulfonic acid;

(5-Chloro-2-{2-[4-(4-fluoro-benzyl)-2R-methyl-piperazin-1-yl]-2-oxo-ethoxy}-pyridin-3-yl)-methanesulfonic acid;

(5-Bromo-2-{2-[4-(4-fluoro-benzyl)-2R-methyl-piperazin-1-yl]-2-oxo-ethoxy}-pyridin-3-yl)-methanesulfonic acid;

(5-Chloro-2-{2-[4-(3,4-difluoro-benzyl)-2R,5S-dimethyl-piperazin-1-yl]-2-oxo-ethoxy}-phenyl)-methanesulfonic acid;

(5-Bromo-2-{2-[4-(3,4-difluoro-benzyl)-2R,5S-dimethyl-piperazin-1-yl]-2-oxo-ethoxy}-phenyl)-methanesulfonic acid;
(5-Chloro-2-{2-[4-(4-chloro-benzyl)-2R-methyl-piperazin-1-yl]-2-oxo-ethoxy}-phenyl)-methanesulfonic acid;
(5-Bromo-2-{2-[4-(4-chloro-benzyl)-2R-methyl-piperazin-1-yl]-2-oxo-ethoxy}-phenyl)-methanesulfonic acid;
(5-Chloro-2-{2-[4-(3,4-difluoro-benzyl)-2R-methyl-piperazin-1-yl]-2-oxo-ethoxy}-phenyl)-methanesulfonic acid;
(5-Bromo-2-{2-[4-(3,4-difluoro-benzyl)-2R-methyl-piperazin-1-yl]-2-oxo-ethoxy}-phenyl)-methanesulfonic acid;
2-(5-Chloro-2-{2-[4-(4-fluoro-benzyl)-2R,5S-dimethyl-piperazin-1-yl]-2-oxo-ethoxy}-phenyl)-ethanesulfonic acid;
(5-Bromo-2-{2-[4-(4-fluoro-benzyl)-2R-methyl-piperazin-1-yl]-2-oxo-ethoxy}-pyridin-3-yl)-ethanesulfonic acid;
(4-Chloro-2-{2-[4-(4-fluoro-benzyl)-2R,5S-dimethyl-piperazin-1-yl]-2-oxo-ethoxy}-phenyl)-methanesulfonic acid;
(3-Bromo-2-{2-[4-(4-fluoro-benzyl)-2R,5S-dimethyl-piperazin-1-yl]-2-oxo-ethoxy}-phenyl)-methanesulfonic acid;
(2-Chloro-6-{2-[4-(4-fluoro-benzyl)-2R,5S-dimethyl-piperazin-1-yl]-2-oxo-ethoxy}-phenyl)-methanesulfonic acid;
(5-Bromo-2-{2-[2R-ethyl-4-(4-fluoro-benzyl)-5S-methyl-piperazin-1-yl]-2-oxo-ethoxy}-phenyl)-methanesulfonic acid;
2-(5-Bromo-2-{2-[4-(4-fluoro-benzyl)-2R,5S-dimethyl-piperazin-1-yl]-2-oxo-ethoxy}-phenyl)-ethanesulfonic acid;
(5-Chloro-2-{2-[4-(4-fluoro-benzyl)-2R-methyl-piperazin-1-yl]-2-oxo-ethoxy}-phenyl)-methanesulfonic acid;
2-(5-Bromo-2-{2-[4-(4-chloro-benzyl)-2R,5S-dimethyl-piperazin-1-yl]-2-oxo-ethoxy}-phenyl)-ethanesulfonic acid;
2-(5-Chloro-2-{2-[4-(3,4-difluoro-benzyl)-2R,5S-dimethyl-piperazin-1-yl]-2-oxo-ethoxy}-phenyl)-ethanesulfonic acid;
2-(5-Chloro-2-{2-[4-(4-chloro-benzyl)-2R-methyl-piperazin-1-yl]-2-oxo-ethoxy}-phenyl)-ethanesulfonic acid;
2-(5-Bromo-2-{2-[4-(4-chloro-benzyl)-2R-methyl-piperazin-1-yl]-2-oxo-ethoxy}-phenyl)-ethanesulfonic acid;
(5-Chloro-2-{2-[4-(4-fluoro-benzyl)-2R,5S-dimethyl-piperazin-1-yl]-2-oxo-ethoxy}-phenyl)-methanesulfonic acid;
2-(5-Chloro-2-{2-[4-(3,4-difluoro-benzyl)-2R-methyl-piperazin-1-yl]-2-oxo-ethoxy}-phenyl)-ethanesulfonic acid;
(5-Bromo-2-{2-[4-(4-chloro-benzyl)-2R-methyl-piperazin-1-yl]-2-oxo-ethoxy}-pyridin-3-yl)-ethanesulfonic acid;
3-(5-Bromo-2-{2-[4-(4-fluoro-benzyl)-2R,5S-dimethyl-piperazin-1-yl]-2-oxo-ethoxy}-phenyl)-propane-1-sulfonic acid;
3-(5-Chloro-2-{2-[4-(4-fluoro-benzyl)-2R-methyl-piperazin-1-yl]-2-oxo-ethoxy}-phenyl)-propane-1-sulfonic acid;
3-(5-Bromo-2-{2-[4-(4-fluoro-benzyl)-2R-methyl-piperazin-1-yl]-2-oxo-ethoxy}-phenyl)-propane-1-sulfonic acid;
(2-Bromo-6-{2-[4-(4-fluoro-benzyl)-2R,5S-dimethyl-piperazin-1-yl]-2-oxo-ethoxy}-phenyl)-methanesulfonic acid;

(5-Chloro-2-{2-[2R-ethyl-4-(4-fluoro-benzyl)-5S-methyl-piperazin-1-yl]-2-oxo-ethoxy}-phenyl)-methanesulfonic acid;
3-(5-Chloro-2-{2-[4-(4-chloro-benzyl)-2R,5S-dimethyl-piperazin-1-yl]-2-oxo-ethoxy}-phenyl)-propane-1-sulfonic acid;
2-(5-Chloro-2-{2-[4-(4-fluoro-benzyl)-2R-methyl-piperazin-1-yl]-2-oxo-ethoxy}-phenyl)-ethanesulfonic acid;
3-(5-Bromo-2-{2-[4-(4-chloro-benzyl)-2R,5S-dimethyl-piperazin-1-yl]-2-oxo-ethoxy}-phenyl)-propane-1-sulfonic acid;
2-(5-Bromo-2-{2-[4-(3,4-difluoro-benzyl)-2R,5S-dimethyl-piperazin-1-yl]-2-oxo-ethoxy}-phenyl)-ethanesulfonic acid;
3-(5-Chloro-2-{2-[4-(3,4-difluoro-benzyl)-2R,5S-dimethyl-piperazin-1-yl]-2-oxo-ethoxy}-phenyl)-propane-1-sulfonic acid;
3-(5-Chloro-2-{2-[4-(4-fluoro-benzyl)-2R,5S-dimethyl-piperazin-1-yl]-2-oxo-ethoxy}-pyridin-3-yl)-propane-1-sulfonic acid;
(5-Bromo-2-{2-[4-(4-fluoro-benzyl)-2R,5S-dimethyl-piperazin-1-yl]-2-oxo-ethoxy}-pyridin-3-yl)-methanesulfonic acid;
3-(5-Chloro-2-{2-[4-(4-chloro-benzyl)-2R-methyl-piperazin-1-yl]-2-oxo-ethoxy}-phenyl)-propane-1-sulfonic acid;
(5-Bromo-2-{2-[4-(3,4-difluoro-benzyl)-2R-methyl-piperazin-1-yl]-2-oxo-ethoxy}-pyridin-3-yl)-ethanesulfonic acid;
(5-Bromo-2-{2-[2R-ethyl-4-(4-fluoro-benzyl)-5S-methyl-piperazin-1-yl]-2-oxo-ethoxy}-phenyl)-ethanesulfonic acid;
3-(5-Bromo-2-{2-[4-(4-chloro-benzyl)-2R-methyl-piperazin-1-yl]-2-oxo-ethoxy}-phenyl)-propane-1-sulfonic acid;
3-(5-Chloro-2-{2-[4-(3,4-difluoro-benzyl)-2R-methyl-piperazin-1-yl]-2-oxo-ethoxy}-phenyl)-propane-1-sulfonic acid;
(5-Bromo-2-{2-[4-(4-fluoro-benzyl)-2R,5S-dimethyl-piperazin-1-yl]-2-oxo-ethoxy}-pyridin-3-yl)-ethanesulfonic acid;
3-(5-Bromo-2-{2-[4-(3,4-difluoro-benzyl)-2R-methyl-piperazin-1-yl]-2-oxo-ethoxy}-phenyl)-propane-1-sulfonic acid;
(2-{2-[4-(4-Fluoro-benzyl)-2R,5S-dimethyl-piperazin-1-yl]-2-oxo-ethoxy}-5-methyl-phenyl)-methanesulfonic acid;
2-(5-Bromo-2-{2-[4-(3,4-difluoro-benzyl)-2R-methyl-piperazin-1-yl]-2-oxo-ethoxy}-phenyl)-ethanesulfonic acid;
3-(5-Chloro-2-{2-[4-(4-fluoro-benzyl)-2R,5S-dimethyl-piperazin-1-yl]-2-oxo-ethoxy}-phenyl)-propane-1-sulfonic acid;
(5-Chloro-2-{2-[4-(4-fluoro-benzyl)-2R,5S-dimethyl-piperazin-1-yl]-2-oxo-ethoxy}-pyridin-3-yl)-methanesulfonic acid;
(5-Bromo-2-{2-[4-(4-fluoro-benzyl)-2R,5S-dimethyl-piperazin-1-yl]-2-oxo-ethoxy}-phenyl)-methanesulfonic acid;
(5-Chloro-2-{2-[4-(3,4-difluoro-benzyl)-2R,5S-dimethyl-piperazin-1-yl]-2-oxo-ethoxy}-pyridin-3-yl)-methanesulfonic acid;
(5-Chloro-2-{2-[4-(4-chloro-benzyl)-2R,5S-dimethyl-piperazin-1-yl]-2-oxo-ethoxy}-pyridin-3-yl)-methanesulfonic acid;
(5-Bromo-2-{2-[4-(4-chloro-benzyl)-2R,5S-dimethyl-piperazin-1-yl]-2-oxo-ethoxy}-pyridin-3-yl)-methanesulfonic acid;

(5-Chloro-2-{2-[4-(3,4-difluoro-benzyl)-2R-methyl-piperazin-1-yl]-2-oxo-ethoxy}-pyridin-3-yl)-methanesulfonic acid;
(5-Bromo-2-{2-[4-(3,4-difluoro-benzyl)-2R-methyl-piperazin-1-yl]-2-oxo-ethoxy}-pyridin-3-yl)-methanesulfonic acid;
(5-Chloro-2-{2-[4-(4-chloro-benzyl)-2R-methyl-piperazin-1-yl]-2-oxo-ethoxy}-pyridin-3-yl)-methanesulfonic acid;
(5-Bromo-2-{2-[4-(4-chloro-benzyl)-2R-methyl-piperazin-1-yl]-2-oxo-ethoxy}-pyridin-3-yl)-methanesulfonic acid;
2-(5-Chloro-2-{2-[4-(4-fluoro-benzyl)-2R,5S-dimethyl-piperazin-1-yl]-2-oxo-ethoxy}-pyridin-3-yl)-ethanesulfonic acid;
(5-Chloro-2-{2-[4-(3,4-difluoro-benzyl)-2R,5S-dimethyl-piperazin-1-yl]-2-oxo-ethoxy}-pyridin-3-yl)-ethanesulfonic acid;
(5-Bromo-2-{2-[4-(3,4-difluoro-benzyl)-2R,5S-dimethyl-piperazin-1-yl]-2-oxo-ethoxy}-pyridin-3-yl)-ethanesulfonic acid;
(5-Chloro-2-{2-[4-(4-chloro-benzyl)-2R,5S-dimethyl-piperazin-1-yl]-2-oxo-ethoxy}-pyridin-3-yl)-ethanesulfonic acid;
(5-Bromo-2-{2-[4-(4-chloro-benzyl)-2R,5S-dimethyl-piperazin-1-yl]-2-oxo-ethoxy}-pyridin-3-yl)-ethanesulfonic acid;
3-(5-Bromo-2-{2-[4-(3,4-difluoro-benzyl)-2R,5S-dimethyl-piperazin-1-yl]-2-oxo-ethoxy}-phenyl)-propane-1-sulfonic acid;
(5-Chloro-2-{2-[4-(4-fluoro-benzyl)-2R-methyl-piperazin-1-yl]-2-oxo-ethoxy}-pyridin-3-yl)-ethanesulfonic acid;
(5-Chloro-2-{2-[4-(3,4-difluoro-benzyl)-2R-methyl-piperazin-1-yl]-2-oxo-ethoxy}-pyridin-3-yl)-ethanesulfonic acid;
(5-Bromo-2-{2-[4-(3,4-difluoro-benzyl)-2R,5S-dimethyl-piperazin-1-yl]-2-oxo-ethoxy}-pyridin-3-yl)-methanesulfonic acid;
(5-Chloro-2-{2-[4-(4-chloro-benzyl)-2R-methyl-piperazin-1-yl]-2-oxo-ethoxy}-pyridin-3-yl)-ethanesulfonic acid;
3-(5-Chloro-2-{2-[4-(4-fluoro-benzyl)-2R,5S-dimethyl-piperazin-1-yl]-2-oxo-ethoxy}-pyridin-3-yl)-propane-1-sulfonic acid;
2-(5-Chloro-2-{2-[4-(4-fluoro-benzyl)-2R,5S-dimethyl-piperazin-1-yl]-2-oxo-ethoxy}-phenyl)-propane-2-sulfonic acid;
2-(5-Bromo-2-{2-[4-(4-fluoro-benzyl)-2R,5S-dimethyl-piperazin-1-yl]-2-oxo-ethoxy}-phenyl)-propane-2-sulfonic acid;
2-(5-Chloro-2-{2-[4-(4-fluoro-benzyl)-2R,5S-dimethyl-piperazin-1-yl]-2-oxo-ethoxy}-phenyl)-2-methyl-propane-1-sulfonic acid;
2-(5-Bromo-2-{2-[4-(4-fluoro-benzyl)-2R,5S-dimethyl-piperazin-1-yl]-2-oxo-ethoxy}-phenyl)-2-methyl-propane-1-sulfonic acid;
1-(5-Chloro-2-{2-[4-(4-fluoro-benzyl)-2R,5S-dimethyl-piperazin-1-yl]-2-oxo-ethoxy}-phenyl)-2-methyl-propane-2-sulfonic acid;
(2-{2-[4-(4-Fluoro-benzyl)-2R,5S-dimethyl-piperazin-1-yl]-2-oxo-ethoxy}-5-trifluoromethyl-phenyl)-methanesulfonic acid;
(2-{2-[4-(4-Fluoro-benzyl)-2R,5S-dimethyl-piperazin-1-yl]-2-oxo-ethoxy}-5-trifluoromethyl-phenyl)-methanesulfonic acid;
(2-{2-[4-(4-Fluoro-benzyl)-2R,5S-dimethyl-piperazin-1-yl]-2-oxo-ethoxy}-5-methyl-phenyl)-methanesulfonic acid;
(5-Chloro-2-{2-[2R-ethyl-4-(4-fluoro-benzyl)-5S-methyl-piperazin-1-yl]-2-oxo-ethoxy}-phenyl)-methanesulfonic acid;
(5-Bromo-2-{2-[2R-ethyl-4-(4-fluoro-benzyl)-5S-methyl-piperazin-1-yl]-2-oxo-ethoxy}-phenyl)-methanesulfonic acid;
(5-Chloro-2-{2-[2R-ethyl-4-(4-fluoro-benzyl)-5S-methyl-piperazin-1-yl]-2-oxo-ethoxy}-phenyl)-ethanesulfonic acid;
(5-Chloro-2-{2-[2R-ethyl-4-(4-fluoro-benzyl)-piperazin-1-yl]-2-oxo-ethoxy}-phenyl)-methanesulfonic acid;
(5-Bromo-2-{2-[2R-ethyl-4-(4-fluoro-benzyl)-piperazin-1-yl]-2-oxo-ethoxy}-phenyl)-methanesulfonic acid;
(5-Chloro-2-{2-[2R-ethyl-4-(4-fluoro-benzyl)-piperazin-1-yl]-2-oxo-ethoxy}-phenyl)-ethanesulfonic acid;
(5-Bromo-2-{2-[2R-ethyl-4-(4-fluoro-benzyl)-piperazin-1-yl]-2-oxo-ethoxy}-phenyl)-ethanesulfonic acid;
1-(5-Bromo-2-{2-[4-(4-fluoro-benzyl)-2R,5S-dimethyl-piperazin-1-yl]-2-oxo-ethoxy}-phenyl)-2-methyl-propane-2-sulfonic acid;
2-(5-Chloro-2-{2-[4-(4-fluoro-benzyl)-2R,5S-dimethyl-piperazin-1-yl]-2-oxo-ethylamino}-phenyl)-ethanesulfonic acid and
(5-Chloro-2-{2-[4-(4-fluoro-benzyl)-2R,5S-dimethyl-piperazin-1-yl]-2-oxo-ethylamino}-phenyl)-methanesulfonic acid;

The present invention also relates to a pharmaceutical composition for treating or preventing a disorder or condition selected from autoimmune diseases, rheumatoid arthritis, recent onset type I diabetes, lupus, inflammatory bowel disease, optic neuritis, psoriasis, multiple sclerosis, polymyalgia rheumatica, uveitis, vasculitis, acute and chronic inflammatory conditions, osteoarthritis, adult Respiratory Distress Syndrome, Respiratory Distress Syndrome of infancy, ischemia reperfusion injury, glomerulonephritis, allergic conditions, asthma, atopic dermatitis, infection associated with inflammation, viral inflammation, influenza, hepatitis, Guillian-Barre, chronic bronchitis, xenotransplantation, chronic and acute transplantation tissue rejection, chronic and acute organ transplant rejection, atherosclerosis, restenosis (including, but not limited to, restenosis following balloon and/or stent insertion), HIV infectivity (co-receptor usage), and granulomatous diseases (including sarcoidosis, leprosy and tuberculosis) and sequelae associated with certain cancers such as multiple myeloma. Compounds in this series may also have utility for the prevention of cancer metastasis. Compounds in this series may also limit the production of cytokines at inflammatory sites, including but not limited to TNF and IL-1, as a consequence of decreasing cell infiltration, providing benefit for diseases linked to TNF and IL-1, including congestive heart failure, pulmonary emphysema or dyspnea associated therewith, emphysema; HIV-1, HIV-2, HIV-3; cytomegalovirus (CMV), adenoviruses, Herpes viruses (*Herpes zoster* and *Herpes simplex*). They may also provide benefit for the sequelae associated with infection where such infection induces production of detrimental inflammatory cytokines such as TNF e.g, fungal meningitis, joint tissue damage, hyperplasia, pannus formation and bone resorption, psoriatic arthritis, hepatic failure, bacterial meningitis, Kawasaki syndrome, myocardial infarction, acute liver failure, lyme disease, septic shock, cancer, trauma, and malaria in a mammal, preferably a human, comprising an amount of a compound of the formula I or a pharmaceutically acceptable salt thereof effective in treating or preventing such disorder or condition and a pharmaceutically acceptable carrier.

The present invention also relates to a pharmaceutical composition for treating or preventing a disorder or condition that can be treated or prevented by inhibiting chemokine binding to the receptor CCR1 in a mammal, preferably a human, comprising an amount of a compound of the formula I, or a pharmaceutically acceptable salt thereof, effective in treating or preventing such disorder or condition and a pharmaceutically acceptable carrier. Examples of such disorders and conditions are those enumerated in the preceding paragraph.

The present invention also relates to a method for treating or preventing a disorder or condition selected from autoimmune diseases, rheumatoid arthritis, recent onset type I diabetes, lupus, inflammatory bowel disease, optic neuritis, psoriasis, multiple sclerosis, polymyalgia rheumatica, uveitis, vasculitis, acute and chronic inflammatory conditions, osteoarthritis, adult Respiratory Distress Syndrome, Respiratory Distress Syndrome of infancy, ischemia reperfusion injury, glomerulonephritis, allergic conditions, asthma, atopic dermatitis, infection associated with inflammation, viral inflammation, influenza, hepatitis, Guillian-Barre, chronic bronchitis, xeno-transplantation, chronic and acute transplantation tissue rejection, chronic and acute organ transplant rejection, atherosclerosis, restenosis (including, but not limited to, restenosis following balloon and/or stent insertion), HIV infectivity (co-receptor usage), and granulomatous diseases (including sarcoidosis, leprosy and tuberculosis) and sequelae associated with certain cancers such as multiple myeloma. Compounds in this series may also have utility for the prevention of cancer metastasis. Compounds in this series may also limit the production of cytokines at inflammatory sites, including but not limited to TNF and IL-1, as a consequence of decreasing cell infiltration, providing benefit for diseases linked to TNF and IL-1, including congestive heart failure, pulmonary emphysema or dyspnea associated therewith, emphysema; HIV-1, HIV-2, HIV-3; cytomegalovirus (CMV), adenoviruses, Herpes viruses (*Herpes zoster* and *Herpes simplex*). They may also provide benefit for the sequelae associated with infection where such infection induces production of detrimental inflammatory cytokines such as TNF e.g, fungal meningitis, joint tissue damage, hyperplasia, pannus formation and bone resorption, psoriatic arthritis, hepatic failure, bacterial meningitis, Kawasaki syndrome, myocardial infarction, acute liver failure, lyme disease, septic shock, cancer, trauma, and malaria in a mammal, preferably a human, comprising administering to a mammal in need of such treatment or prevention an amount of a compound of the formula I, or a pharmaceutically acceptable salt thereof, that is effective in treating or preventing such disorder or condition.

The present invention also relates to a method for treating or preventing a disorder or condition that can be treated or prevented by antagonizing the CCR1 receptor in a mammal, preferably a human, comprising administering to a mammal in need of such treatment or prevention an amount of a compound of the formula I, or a pharmaceutically acceptable salt thereof, that is effective in treating or preventing such disorder or condition.

The present invention also relates to a pharmaceutical composition for treating or preventing a disorder or condition selected from autoimmune diseases, rheumatoid arthritis, recent onset type I diabetes, lupus, inflammatory bowel disease, optic neuritis, psoriasis, multiple sclerosis, polymyalgia rheumatica, uveitis, vasculitis, acute and chronic inflammatory conditions, osteoarthritis, adult Respiratory Distress Syndrome, Respiratory Distress Syndrome of infancy, ischemia reperfusion injury, glomerulonephritis, allergic conditions, asthma, atopic dermatitis, infection associated with inflammation, viral inflammation, influenza, hepatitis, Guillian-Barre, chronic bronchitis, xeno-transplantation, chronic and acute transplantation tissue rejection, chronic and acute organ transplant rejection, atherosclerosis, restenosis, restenosis (including, but not limited to, restenosis following balloon and/or stent insertion), HIV infectivity (co-receptor usage), and granulomatous diseases (including sarcoidosis, leprosy and tuberculosis) and sequelae associated with certain cancers such as multiple myeloma. Compounds in this series may also have utility for the prevention of cancer metastasis. Compounds in this series may also limit the production of cytokines at inflammatory sites, including but not limited to TNF and IL-1, as a consequence of decreasing cell infiltration, providing benefit for diseases linked to TNF and IL-1, including congestive heart failure, pulmonary emphysema or dyspnea associated therewith, emphysema; HIV-1, HIV-2, HIV-3; cytomegalovirus (CMV), adenoviruses, Herpes viruses (*Herpes zoster* and *Herpes simplex*). They may also provide benefit for the sequelae associated with infection where such infection induces production of detrimental inflammatory cytokines such as TNF e.g, fungal meningitis, joint tissue damage, hyperplasia, pannus formation and bone resorption, psoriatic arthritis, hepatic failure, bacterial meningitis, Kawasaki syndrome, myocardial infarction, acute liver failure, lyme disease, septic shock, cancer, trauma, and malaria in a mammal, preferably a human, comprising a CCR1 receptor antagonizing effective amount of a compound of the formula I, or a pharmaceutically acceptable salt thereof, and a pharmaceutically acceptable carrier.

The present invention also relates to a pharmaceutical composition for treating or preventing a disorder or condition that can be treated or prevented by antagonizing the CCR1 receptor in a mammal, preferably a human, comprising a CCR1 receptor antagonizing effective amount of a compound of the formula I, or a pharmaceutically acceptable salt thereof, and a pharmaceutically acceptable carrier.

The present invention also relates to a method for treating or preventing a disorder or condition selected from autoimmune diseases, rheumatoid arthritis, recent onset type I diabetes, lupus, inflammatory bowel disease, optic neuritis, psoriasis, multiple sclerosis, polymyalgia rheumatica, uveitis, vasculitis, acute and chronic inflammatory conditions, osteoarthritis, adult Respiratory Distress Syndrome, Respiratory Distress Syndrome of infancy, ischemia reperfusion injury, glomerulonephritis, allergic conditions, asthma, atopic dermatitis, infection associated with inflammation, viral inflammation, influenza, hepatitis, Guillian-Barre, chronic bronchitis, xeno-transplantation, chronic and acute transplantation tissue rejection, chronic and acute organ transplant rejection, atherosclerosis, restenosis (including, but not limited to, restenosis following balloon and/or stent insertion), HIV infectivity (co-receptor usage), and granulomatous diseases (including sarcoidosis, leprosy and tuberculosis) and sequelae associated with certain cancers such as multiple myeloma. Compounds in this series may also have utility for the prevention of cancer metastasis. Compounds in this series may also limit the production of cytokines at inflammatory sites, including but not limited to TNF and IL-1, as a consequence of decreasing cell infiltration, providing benefit for diseases linked to TNF and IL-1, including congestive heart failure, pulmonary emphysema or dyspnea associated therewith, emphysema; HIV-1, HIV-2, HIV-3; cytomegalovirus (CMV), adenoviruses, Herpes viruses (*Herpes zoster* and *Herpes simplex*). They may also provide benefit for the sequelae associated with infection where such infection induces production of detrimental inflammatory cytokines such as TNF e.g, fungal meningitis, joint tissue damage, hyperplasia, pannus formation and bone resorption, psoriatic arthritis, hepatic failure, bacterial meningitis, Kawasaki syndrome, myocardial infarction, acute liver failure, lyme disease, septic shock, cancer, trauma, and malaria in a mammal, preferably a human, comprising administering to a mammal in need of such treatment or prevention a CCR1 receptor antagonizing effective amount of a compound of formula I, or a pharmaceutically acceptable salt thereof.

DETAILED DESCRIPTION OF THE INVENTION

The following reaction Schemes illustrate the preparation of the compounds of the present invention. Unless otherwise indicated a, b, c, d and $R^1$ through $R^6$ and structural formula I in the reaction Schemes and the discussion that follow are defined as above.

The reactions in the Preparations and Schemes are described in commonly assigned copending provisional applications Ser. No. 60/193789, filed Mar. 31, 2000, Ser. No. 60/241804 filed Oct. 19, 2000 and Ser. No. 09/821322 now U.S. Pat. No. 6,649,161, filed Mar. 29, 2001, the disclosure of which is incorporated herein by reference thereto.

PREPARATION A

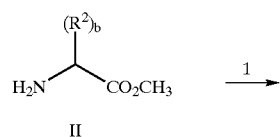

II

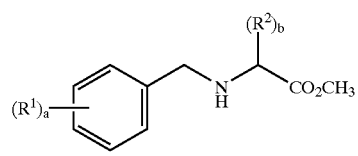

III

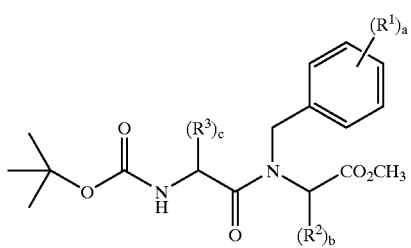

IV

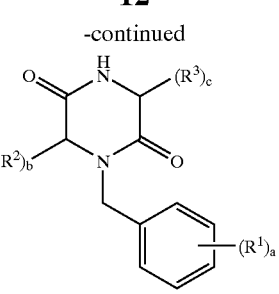

V

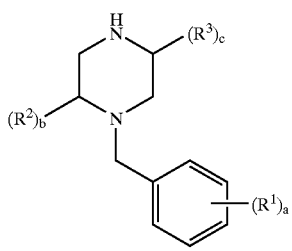

VI

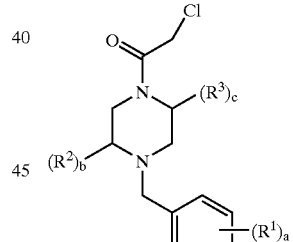 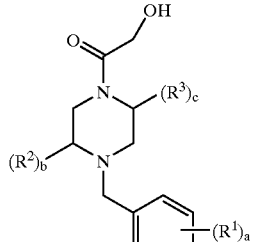

VII  VIII

PREPARATION B

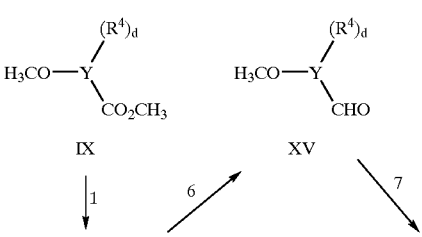

IX  XV

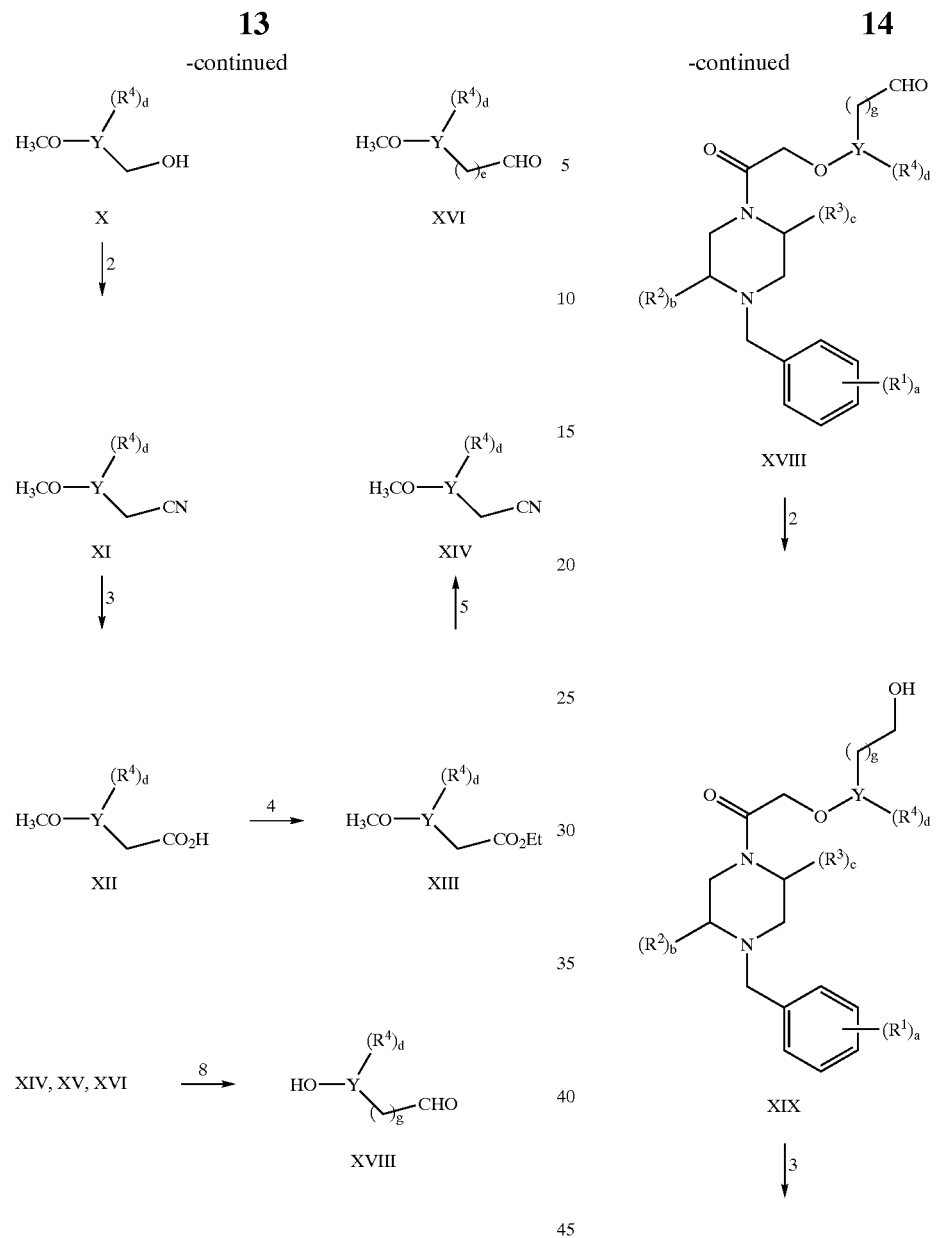
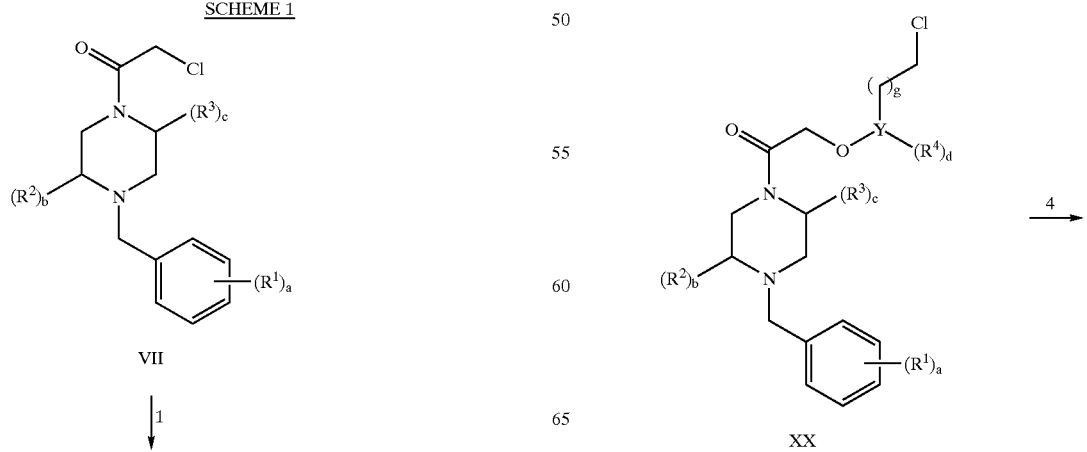

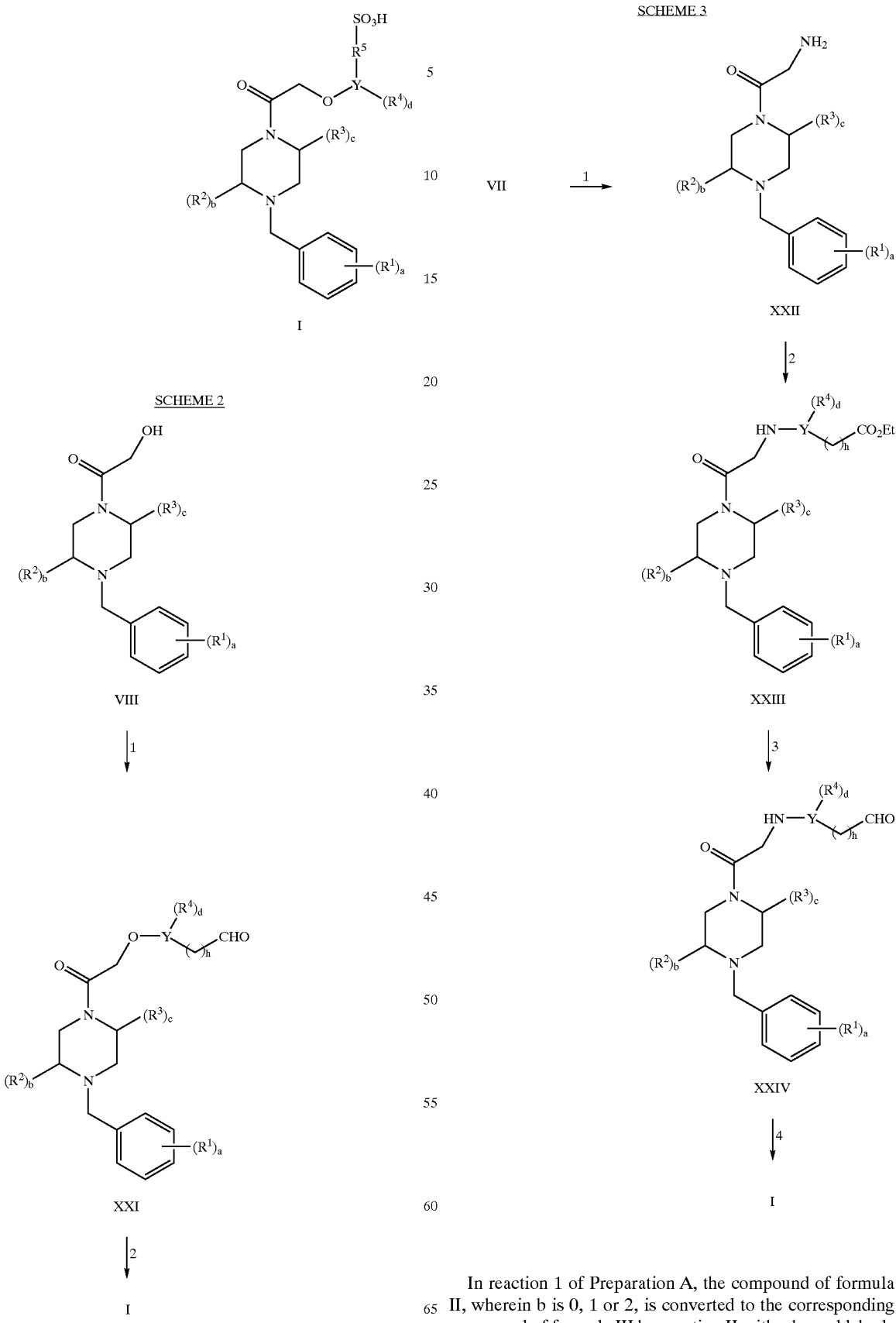
In reaction 1 of Preparation A, the compound of formula II, wherein b is 0, 1 or 2, is converted to the corresponding compound of formula III by reacting II with a benzaldehyde compound of the formula

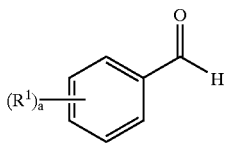

in the presence of a base, such as triethylamine, and a reducing agent, such as sodium triacetoxyborohydride, in an aprotic solvent, such as 1,2-dichloroethane. The reaction mixture is stirred at room temperature for a time period between about 1 hour to about 4 hours, preferably about 2 hours.

In reaction 2 of Preparation A, the compound of formula III is converted to the corresponding compound of formula IV by first reacting a compound of the formula

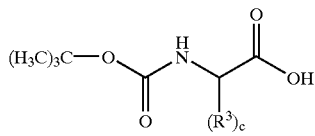

wherein c is 0, 1 or 2, with 4-methyl morpholine and isobutylchloroformate in the presence of a polar aprotic solvent, such as tetrahydrofuran, followed by reacting the intermediate so formed with the compound of formula III. The reaction mixture, so formed, is stirred overnight at ambient temperature.

In reaction 3 of Preparation A, the compound of formula IV is converted to the corresponding piperizine-2,5-dione compound of formula V by treating IV with trifluoroacetic acid in the presence of a polar aprotic solvent, such as methylene chloride. The reaction is stirred, at room temperature, for a time period between about 1 hour to about 4 hours, preferably about 2 hours.

In reaction 4 of Preparation A, the compound of formula V is converted to the corresponding compound of formula VI by reducing V with a reducing agent, such as lithium aluminum hydride. The reaction is conducted at a temperature between about −10° C. to about 10° C., preferably about 0° C., for a time period between about 10 minutes to about 90 minutes, preferably about 40 minutes.

In reaction 5 of Preparation A, the compound of formula VI is converted to the corresponding compound of formula VII by reacting VI with chloroacetyl chloride in the presence of a base, such as triethylamine, in a polar aprotic solvent, such as methylene chloride, at ambient temperature for a time period between 15 minutes and 3 hours, preferably about 30 minutes.

In reaction 6 of Preparation A, the compound of formula VI is converted to the corresponding compound of formula VIII by reacting VI with acetoxy acetylchloride in the presence of a base, such as triethylamine, in a polar aprotic solvent, such as methylene chloride, at ambient temperature for a time period between 15 minutes and 4 hours, preferably about 1 hour. The resulting acetyl-protected alcohol is reacted with lithium hydroxide hydrate in a solvent mixture including water, tetrahydrofuran and methanol, at ambient temperature for a time period between 1 hour and 8 hours, preferably about 2 hours.

In reaction 1 of Preparation B the compound of formula IX is converted to the corresponding compound of the formula X by treating IX with a reducing agent, such as lithium aluminum hydride, in an aprotic solvent, such as tetrahydrofuran. The reaction mixture is heated to reflux for a time period between 1 hour and 6 hours, preferably about 2 hours.

In reaction 2 of Preparation B the compound of formula X is converted to the corresponding compound of the formula XI by first converting the hydroxyl group to a chloro group by reacting X with thionyl chloride, in the presence of an aprotic solvent, such as methylene chloride. The reaction is heated to reflux, for a time period between about 1 hour to about 10 hours, preferably about 3 hours. The resulting alkyl chloride is then treated with a cyanide source, such as potassium cyanide, in the presence of an aprotic solvent, such as acetonitrile and a crown ether, such as 18-crown-6. The reaction mixture is stirred at ambient temperature for a time period between about 1 hour to about 10 hours, preferably about 3 hours.

In reaction 3 of Preparation B the compound of formula XI is converted to the compound of formula XII by first treating XI with a hydroxide source, such as potassium hydroxide in a mixture of ethanol and water. The reaction mixture is heated to reflux for a time period between about 1 hour to about 10 hours, preferably about 8 hours.

In reaction 4 of Preparation B the compound of formula XII is converted to the compound of formula XIII by treating with ethanol in the presence of an acid, such as hydrochloric acid, at ambient temperature for a time period between about 8 hours to about 16 hours, preferably about 12 hours.

In reaction 5 of Preparation B the compound of formula XIII is converted to the corresponding compound of formula XIV, by first treating XIII with an reducing agent, as above in reaction 1 of Preparation B. The resultant alcohol may be converted to XIV with an oxidizing agent, such as Dess-Martin periodinane, in the presence of an aprotic solvent, such as tetrahydrofuran at ambient temperature for a time period between about 1 hour to about 16 hours, preferably about 4 hours.

In reaction 6 of Preparation B the compound of formula X is converted to the corresponding compound of formula XV by first treating X with an oxidizing agent, such as Dess-Martin periodinane, in the presence of an aprotic solvent, such as tetrahydrofuran at ambient temperature for a time period between about 1 hour to about 16 hours, preferably about 4 hours.

In reaction 7 of Preparation B the compound of formula XV is converted to the corresponding compound of formula XVI, wherein e may equal 2–7, by first treating XV with a phosphonium ylide derived from the phosphonium salt of the formula:

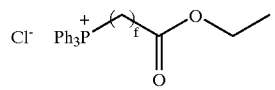

wherein f may be $(C_{1-6})$-alkyl, wherein alkyl is defined as above, in the presence of an aprotic solvent, such as tetrahydrofuran. The reaction is conducted at a temperature between −78° C. and reflux, the preferred temperature is dependent on which phosphonium ylide is utilized, for a time period between about 4 hours to about 16 hours, preferably about 10 hours (For similar transformations, see: J. Am. Chem. Soc. 1985, 107, 217). The resulting olefinic ester is then hydrogenated by shaking under a positive pressure of hydrogen in the presence of a catalyst, such as platinum dioxide, in the presence of an aprotic solvent such as ethyl acetate. The ester is then reduced and reoxidized according to the procedure described in reaction 5 of Preparation B to afford compound of formula XVI.

In reaction 8 of Preparation C compounds of formula XIV, XV or XVI are converted to the corresponding compound of formula XVIII, wherein g equals 0–7, by demethylating the methyl ether with acid, such as 47% aqueous hydrogen bromide. The reaction mixture is heated to reflux for a time period between about 10 hours to about 30 hours, preferably about 24 hours.

In reaction 1 of Scheme 1, the compound of formula VII is converted to the corresponding compound of formula XVIII, wherein g equals 0–7, by reacting VII with a compound of the formula XVII in the presence of potassium carbonate, potassium iodide and an aprotic solvent, such as dimethylformamide. The reaction is heated to reflux for a time period between about 4 hours to about 8 hours, preferably about 6 hours.

In reaction 2 of Scheme 1, the compound of formula XVIII is converted to the corresponding compound of formula XIX, wherein g equals 0–7, by reacting XVIII with a reducing agent, such as sodium borohydride, in an aprotic solvent, such as tetrahydrofuran, at a temperature between about –10° C. and ambient temperature, preferably ambient for a time period between 15 minutes and 90 minutes, preferably about 60 minutes.

In reaction 3 of Scheme 1, the compound of formula XIX is converted to the corresponding compound of formula XX, wherein g equals 0–7, as described in reaction 2 of preparation B.

In reaction 4 of Scheme 1, the compound of formula XX is converted to the corresponding compound of formula I by reacting XX with sodium sulfite in water, at a temperature between 70° C. and 100° C., preferably 100° C. for a time period between 1 and 5 hours, preferably about 1 hour. The addition of catalytic sodium iodide may be advantageous.

In reaction 1 of Scheme 2, the compound of formula VIII is converted to the corresponding compound of formula XXI by reacting VIII with a compound of formula

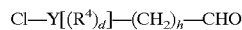

where Y is a (C2–C9) heteroaryl wherein the chlorine is attached to a carbon atom that is adjacent to a heteroatom (for example, 2-pyridyl)and wherein h equals 0–7. The reactants are stirred in a polar aprotic solvent, such as acetonitrile, in the presence of a base, such as triethylamine, at reflux temperature for a time period between about 4 hours and 24 hours, preferably about 12 hours.

In reaction 2 of Scheme 2, the compound of formula XXI, where Y is a (C2–C9) heteroaryl, may be converted into I using the methodologies described above in Scheme 1.

In reaction 1 of Scheme 3, the compound of formula VII may be converted to the corresponding compound of formula XXII, where Y is a (C2–C9) heteroaryl, by reacting VII with tert-butoxycarbonylamino-acetic acid in an aprotic solvent, such as methylene chloride, with a carbodiimide, such dicyclohexylcarbodiimide, in the presence of a base, such as triethylamine, at room temperature for a time period between about 1 and 24 hours, preferably about 3 hours. The compound of formula XXII may subsequently be produced from this carbamate by the action of trifluoroacetic acid at room temperature for a time period between about 1 and 12 hours, preferably about 4 hours.

In reaction 2 of Scheme 3, the compound of formula XXII may be converted to the corresponding compound of formula XXIII, where Y is a ($C_2$–$C_9$) heteroaryl, following the precedent set forth in reaction 1 of Scheme 2.

In reaction 3 of Scheme 3, the compound of formula XXIII may be converted to the corresponding compound of formula XXIV, where Y is a ($C_2$–$C_9$) heteroaryl, by first reducing the ester to the corresponding alcohol with a reducing agent, such as sodium borohydride, in tert-butanol and methanol, at a temperature between about 20° C. and reflux, preferably reflux for a time period between 1 hour and 6 hours, preferably about 1 hour. The resultant alcohol may be converted to the compound of formula XXIV by treating with an oxidizing agent, such as Dess-Martin periodinane, in the presence of an aprotic solvent, such as tetrahydrofuran at ambient temperature for a time period between about 1 hour to about 16 hours, preferably about 4 hours.

In reaction 4 of Scheme 3, the compound of formula XXIV, where Y is a ($C_2$–$C_9$) heteroaryl, may be converted into I using the methodologies described above in Scheme 1.

Unless indicated otherwise, the pressure of each of the above reactions is not critical. Generally, the reactions will be conducted at a pressure of about one to about three atmospheres, preferably at ambient pressure (about one atmosphere).

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, a solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate (i.e., 1,1'-methylene-bis-(2-hydroxy-3-naphthoate)) salts.

Those compounds of the formula I which are also acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

Compounds of the formula I and their pharmaceutically acceptable salts (hereinafter also referred to, collectively, as "the active compounds") are potent antagonists of the CCR1 receptor. The active compounds are useful in the treatment or prevention of autoimmune diseases (such as rheumatoid arthritis, type I diabetes (recent onset), lupus, inflammatory bowel disease, optic neuritis, psoriasis, multiple sclerosis, polymyalgia rheumatica, uveitis, and vasculitis), acute and chronic inflammatory conditions (such as osteoarthritis, adult Respiratory Distress Syndrome, Respiratory Distress Syndrome of infancy, ischemia reperfusion injury, glomerulonephritis, and chronic obstructive pulmonary disease (COPD)), allergic conditions (such as asthma and atopic dermatitis), inflammation associated with infection (such as viral inflammation (including influenza, hepatitis and Guillian-Barre), chronic bronchitis, chronic and acute tissue, cell, and solid organ transplant rejection (including xeno-transplantation), atherosclerosis, restenosis, HIV infectivity (co-receptor usage), and granulomatous diseases (including sarcoidosis, leprosy and tuberculosis) and sequelae associated with certain cancers such as multiple myeloma. Compounds in this series may also have utility for the prevention of cancer metastasis, as well as restenosis following balloon and/or stent insertion. Compounds in this series may also limit the production of cytokines at inflammatory sites, including but not limited to TNF and IL-1, as a consequence of decreasing cell infiltration, providing benefit for diseases linked to TNF and IL-1 including congestive heart failure, pulmonary emphysema or dyspnea associated therewith, emphysema; HIV-1, HIV-2, HIV-3; cytomegalovirus (CMV), adenoviruses, Herpes viruses (*Herpes zoster* and *Herpes simplex*). They may also provide benefit for the sequelae associated with infection where such infection induces production of detrimental inflammatory cytokines such as TNF e.g, fungal meningitis, joint tissue damage, hyperplasia, pannus formation and bone resorption, psoriatic arthritis, hepatic failure, bacterial meningitis, Kawasaki syndrome, myocardial infarction, acute liver failure, lyme disease, septic shock, cancer, trauma, and malaria, etc.

The activity of the compounds of the invention can be assessed according to procedures know to those of ordinary skill in the art. Examples of recognized methods for determining CCR1 induced migration can be found in Coligan, J. E., Kruisbeek, A. M., Margulies, D. H., Shevach, E. M., Strober, W. editors: *Current Protocols In Immunology,* 6.12.1–6.12.3. (John Wiley and Sons, NY, 1991). One specific example of how to determine the activity of a compound for inhibiting migration is described in detail below.

Chemotaxis Assay:

The ability of compounds to inhibit the chemotaxis to various chemokines can be evaluated using standard 48 or 96 well Boyden Chambers with a 5 micron polycarbonate filter. All reagents and cells can be prepared in standard RPMI (BioWhitikker Inc.) tissue culture medium supplemented with 1 mg/mL of bovine serum albumin. Briefly, MIP-1α (Peprotech, Inc., P.O. Box 275, Rocky Hill N.J.) or other test agonists, are placed into the lower chambers of the Boyden chamber. A polycarbonate filter is then applied and the upper chamber fastened. The amount of agonist chosen is that determined to give the maximal amount of chemotaxis in this system (e.g., 1 nM for MIP-1α should be adequate).

THP-1 cells (ATCC TIB-202), primary human monocytes, or primary lymphocytes, isolated by standard techniques can then be added to the upper chambers in triplicate together with various concentrations of the test compound. Compound dilutions can be prepared using standard serological techniques and are mixed with cells prior to adding to the chamber.

After a suitable incubation period at 37 degrees centigrade (e.g. 3.5 hours for THP-1 cells, 90 minutes for primary monocytes), the chamber is removed, the cells in the upper chamber aspirated, the upper part of the filter wiped and the number of cells migrating can be determined according to the following method.

For THP-1 cells, the chamber (a 96 well variety manufactured by Neuroprobe) can be centrifuged to push cells off the lower chamber and the number of cells can be quantitated against a standard curve by a color change of the dye fluorocein diacetate.

For primary human monocytes, or lymphocytes, the filter can be stained with Dif Quik® dye (American Scientific Products) and the number of cells migrating can be determined microscopically.

The number of cells migrating in the presence of the compound are divided by the number of cells migrating in control wells (without the compound). The quotant is the % inhibition for the compound which can then be plotted using standard graphics techniques against the concentration of compound used. The 50% inhibition point is then determined using a line fit analysis for all concentrations tested. The line fit for all data points must have an coefficient of correlation (R squared) of >90% to be considered a valid assay.

All of the compounds of the invention illustrated in the following examples had $IC_{50}$ of less than 10 μM, in the Chemotaxis assay.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation. The active compounds of the invention may also be formulated for sustained delivery.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion.

Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., rheumatoid arthritis) is 0.1 to 1000 mg of the active ingredient per unit dose which could be administered, for example, 1 to 4 times per day.

Aerosol formulations for treatment of the conditions referred to above (e.g., rheumatoid arthritis) in the average adult human are preferably arranged so that each metered dose or "puff" of aerosol contains 20 µg to 1000 µg of the compound of the invention. The overall daily dose with an aerosol will be within the range 0.1 mg to 1000 mg. Administration may be several times daily, for example 2, 3, 4 or 8 times, giving for example, 1, 2 or 3 doses each time.

The active agents can be formulated for sustained delivery according to methods well known to those of ordinary skill in the art. Examples of such formulations can be found in U.S. Pat. Nos. 3,538,214, 4,060,598, 4,173,626, 3,119,742, and 3,492,397.

The compounds of the invention can also be utilized in combination therapy with immunosuppressant agents including but not limited to rapamycin, cyclosporin A, FK-506, Cellcept®; azathioprine, and IL-2R inhibitory antibodies or with classical anti-inflammatory agents (e.g. cyclooxygenase/lipoxygenase inhibitors) such as but not limited to, aspirin, acetaminophen, naproxen and piroxicam or with cytokine inhibitory agents including but not limited to ENBREL.

The following Examples illustrate the preparation of the compounds of the present invention. Commercial reagents were utilized without further purification. Chromatography refers to column chromatography performed using 32–63 mm silica gel and executed under nitrogen pressure (flash chromatography) conditions. Particle Beam Mass Spectra were recorded on either a Hewlett Packard 5989®, utilizing chemical ionization (ammonium), or a Fisons (or MicroMass) Atmospheric Pressure Chemical Ionization (APCI) platform which uses a 50/50 mixture of acetonitrile/water. Room or ambient temperature refers to 20–25° C. All non-aqueous reactions were run under a nitrogen atmosphere for convenience and to maximize yields. Concentration in vacuo means that a rotary evaporator was used. The names for the compounds of the invention were created by the Autonom 2.0 PC-batch version from Beilstein Informationssysteme GmbH (ISBN 3-89536-976-4)

EXAMPLE 1

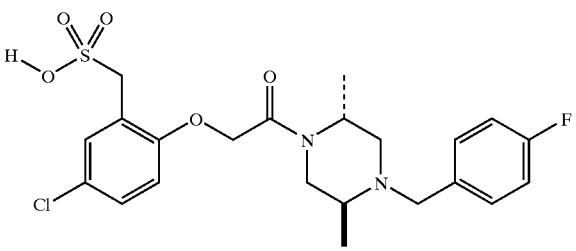

(5-Chloro-2-{2-[4-(4-fluoro-benzyl)-(2R,5S)-2,5-dimethyl-piperazin-1-yl]-2-oxo-ethoxy}-phenyl)-methanesulfonic acid (S)-2-(4-Fluoro-benzylamino)-propionic acid methyl ester To a solution of (S)-2-amino-propionic acid methyl ester hydrochloride (25 g, 179 mmol) and 4-fluorobenzaldehyde (23 mL, 215 mmol) in 1,2-dichloroethane (200 mL) was added triethylamine (25 mL, 179 mmol). The resulting mixture was stirred for two hours at ambient temperature followed by addition of sodium triacetoxyborohydride (57 g, 268 mmol) in four portions. The resulting mixture was stirred overnight at ambient temperature. The reaction was neutralized with dilute aqueous sodium hydroxide solution and extracted with dichloromethane. The organic layer was dried over magnesium sulfate, filtered and concentrated in vacuo. Chromatography on silica gel gave the title compound (34.4 g).

(2S)-2-[(2R)-(2-tert-Butoxycarbonylamino-propionyl)-(4-fluoro-benzyl)-amino]-propionic acid methyl ester To a solution of (R)-2-tert-butoxycarbonylamino-propionic acid (37 g, 195 mmol) in dry tetrahydrofuran (250 mL) at 0° C. was added 4-methyl morpholine (21.5 mL, 195 mmol) followed by isobutylchloroformate (25.3 mL, 195 mmol). The reaction was allowed to warm to ambient temperature and stirred for two hours. This was followed by the addition of (S)-2-(4-fluoro-benzylamino)-propionic acid methyl ester (34.4 g, 162 mmol). The resulting mixture was stirred overnight at ambient temperature. The reaction mixture was filtered through a pad of celite and the filter cake was washed with ethyl acetate. The filtrate was concentrated in vacuo, diluted with ethyl acetate and washed with water and brine. The organic layer was dried over magnesium sulfate, filtered and concentrated in vacuo. Chromatography on silica gel gave the title compound (43.2 g).

(3R,6S)-1-(4-Fluoro-benzyl)-3,6-dimethyl-piperazine-2,5-dione

To a solution of (2S)-2-[(2R)-(2-tert-butoxycarbonylamino-propionyl)-(4-fluoro-benzyl)-amino]-propionic acid methyl ester (43 g, 382 mmol) in dichloromethane (120 mL) at 0° C. was added trifluoroacetic acid (60 mL). The reaction was allowed to warm to ambient temperature and stirred for 2 hours. The reaction was cooled to 0° C. and slowly quenched by addition of 3 N sodium hydroxide until basic. The resulting mixture was extracted with dichloromethane. The organic layer was dried over magnesium sulfate, filtered and concentrated in vacuo to give the title compound (22 g).

(2R,5S)-1-(4-Fluoro-benzyl)-2,5-dimethyl-piperazine

To a solution of (3R,6S)-1-(4-fluoro-benzyl)-3,6-dimethyl-piperazine-2,5-dione (22 g, 87.9 mmol) in dry tetrahydrofuran (160 mL) at 0° C. was added a solution of lithium aluminum hydride (1M in tetrahydrofuran, 373 mL, 373 mmol) dropwise over 40 minutes. The reaction mixture was then refluxed for 4 hours, cooled to ambient temperature and slowly quenched with water. The resulting mixture was filtered through a pad of celite and the filter cake was washed with ethyl acetate. The filtrate was then concentrated, diluted with ethyl acetate and washed with saturated aqueous sodium hydrogen carbonate. The organic layer was separated, dried over magnesium sulfate, filtered and concentrated in vacuo to give the title compound (17.7 g).

2-Chloro-1-[4-(4-fluoro-benzyl)-(2R,5S)-2,5-dimethyl-piperazin-1-yl]-ethanone

To a solution of (2R,5S)-1-(4-fluoro-benzyl)-2,5-dimethyl-piperazine (2.5 g, 11.2 mmol) in dry dichloromethane (11 mL) at 0° C. was added triethylamine (1.57 mL, 11.2 mmol) followed by chloroacetyl chloride (0.86 mL, 11.2 mmol). The resulting reaction mixture was stirred for 30 minutes. The reaction was then filtered through a pad of celite, washed with dichloromethane and the resulting filtrate was concentrated. Chromatography on silica gel gave the title compound (2.84 g).

5-Chloro-2-{2-[4-(4-fluoro-benzyl)-(2R,5S)-2,5-dimethyl-piperazin-1-yl]-2-oxo-ethoxy}-benzaldehyde To a solution of 2-chloro-1-[4-(4-fluoro-benzyl)-(2R,5S)-2,5-dimethyl-piperazin-1-yl]-ethanone (2.87 g, 9.6 mmol) in dimethylformamide (20 mL) was added 5-chlorosalicylaldehyde (1.65 g, 10.5 mmol), potassium carbonate (2.64 g, 19.2 mmol) and potassium iodide (1.59 g, 9.6 mmol). The resulting mixture was heated to 100° C. for 12 hours. The reaction was cooled, diluted with saturated aqueous brine and extracted with ethyl acetate. The organic layer was dried over magnesium sulfate and filtered. The filtrate was concentrated in vacuo to give crude product. Purification via chromatography on silica gel gave the title compound (3.40 g).

2-(4-Chloro-2-hydroxymethyl-phenoxy)-1-[4-(4-fluoro-benzyl)-(2R,5S)-2,5-dimethyl-piperazin-1-yl]-ethanone To a solution of 5-chloro-2-{2-[4-(4-fluoro-benzyl)-(2R,5S)-2,5-dimethyl-piperazin-1-yl]-2-oxo-ethoxy}-benzaldehyde (0.99 g, 2.36 mmol) in dry methanol (25 mL) was added sodium borohydride (0.19 g, 4.92 mmol). After 1 hour the reaction was acidified to pH 2 by the addition of 1N hydrochloric acid. After 5 minutes the reaction was neutralized with 1N sodium hydroxide and the methanol removed by evaporation. The resulting aqueous suspension was extracted with ethyl acetate. The organic layer was washed with brine, dried over magnesium sulfate, filtered and evaporated to give the title compound (0.98 g).

2-(4-Chloro-2-chloromethyl-phenoxy)-1-[4-(4-fluoro-benzyl)-2,5-dimethyl-piperazin-1-yl]-ethanone To 2-(4-chloro-2-hydroxymethyl-phenoxy)-1-[4-(4-fluoro-benzyl)-(2R,5S)-2,5-dimethyl-piperazin-1-yl]-ethanone (0.55 g, 1.3 mmol) in methylene chloride (6 ml) was added thionyl chloride (0.26 ml, 3.58 mmol). The reaction was heated to reflux for 2 hours. After cooling the reaction was quenched by the addition of water. The organic layer was washed with saturated sodium bicarbonate followed by saturated aqueous sodium chloride. The organic layer was then concentrated to afford the title compound as a yellow oil (0.52 g).

(5-Chloro-2-{2-[4-(4-fluoro-benzyl)-(2R,5S)-2,5-dimethyl-piperazin-1-yl]-2-oxo-ethoxy}-phenyl)-methanesulfonic acid To 2-(4-chloro-2-chloromethyl-phenoxy)-1-[4-(4-fluoro-benzyl)-2R,5S-dimethyl-piperazin-1-yl]-ethanone (0.52 g, 1.2 mmol) in 1:1 ethanol:water (6 mL) was added sodium sulfite (0.75 g, 5.97 mmol). The reaction was heated to reflux for 12 hours. After cooling the reaction was concentrated and purified by chromatography on silica gel to afford the title compound (0.39 g) as a sodium salt.

EXAMPLE 2

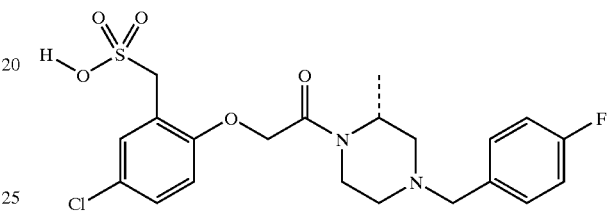

(5-Chloro-2-{2-[4-(4-fluoro-benzyl)-2R-methyl-piperazin-1-yl]-2-oxo-ethoxy}-phenyl)-methanesulfonic acid (3R)-1-(4-Fluoro-benzyl)-3-methyl-piperazine To a solution of (2R)-2-methyl-piperazine (4.5 g, 45 mmol) in ethanol (80 mL) was added 4-fluorobenzyl chloride (5.38 mL, 45.0 mmol) and sodium hydrogen carbonate (11.3 g, 135 mmol). The reaction was refluxed overnight, cooled and concentrated. The remaining residue was diluted with dichloromethane and washed with water. The organic layer was separated and concentrated to give a clear oil. Chromatography on silica gel gave the title compound (5.0 g).

2-Chloro-1-[4-(4-fluoro-benzyl)-2R-methyl-piperazin-1-yl]-ethanone

To a solution of (3R)-1-(4-fluoro-benzyl)-3-methyl-piperazine (3 g, 14.4 mmol) in dichloromethane (40 mL) was added triethylamine (2.0 mL, 14.4 mmol). The reaction was cooled to 0° C. and chloroacetyl chloride was added (1.1 mL, 14.4 mmol). The reaction was allowed to warm to ambient temperature and stirred for 2 hours. The reaction was diluted with dichloromethane and washed with 10% citric acid. The organic layer was separated, dried over magnesium sulfate, filtered and concentrated in vacuo. Chromatography on silica gel gave the title compound (3.9 g).

5-Chloro-2-{2-[4-(4-fluoro-benzyl)-2R-methyl-piperazin-1-yl]-2-oxo-ethoxy}-benzaldehyde To a solution of 2-chloro-1-[4-(4-fluoro-benzyl)-2R-methyl-piperazin-1-yl]-ethanone (0.1g. 0.352 mmol) in dimethylformamide (5 mL) was added 5-chlorosalicylaldehyde (60 mg, 0.387 mmol), potassium carbonate (97 mg, 0.704 mmol) and potassium iodide (58 mg, 0.352 mmol). The resulting mixture was heated to 65° C. for 2 hours. The reaction was cooled and the dimethylformamide was removed in vacuo. The crude reaction was diluted with ethyl acetate, washed with saturated aqueous and the organic layer was dried over magnesium sulfate and filtered. The filtrate was concentrated in vacuo to give the title compound (140 mg) which was used directly in the following step.

(5-Chloro-2-{2-[4-(4-fluoro-benzyl)-2R-methyl-piperazin-1-yl]-2-oxo-ethoxy}-phenyl)-methanesulfonic acid To a solution of 5-chloro-2-{2-[4-(4-fluoro-benzyl)-2R-methyl-piperazin-1-yl]-2-oxo-ethoxy}-benzaldehyde (90 mg, 0.223 mmol) in tetrahydrofuran (2 mL) was added sodium borohydride (25 mg, 0.667 mmol). After 1 hour the reaction was diluted with ethyl actate and washed with water followed by brine. The organic layer was dried over magnesium sulfate, filtered and concentrated in vacuo to afford the corresponding alcohol, which was taken on to the next step.

To 2-(4-chloro-2-hydroxymethyl-phenoxy)-1-[4-(4-fluoro-benzyl)-2R,-methyl-piperazin-1-yl]-ethanone (0.223 mmol) in methylene chloride (3 ml) was added thionyl chloride (0.04 ml, 0.558 mmol). The reaction was heated to reflux for 1 hour. After cooling the reaction was diluted with additional methylene chloride, washed with saturated aqueous sodium bicarbonate followed by brine. The organic layer was then dried over magnesium sulfate and concentrated in vacuo to afford the corresponding chloride as a yellow oil, which was taken on to the next step.

To 2-(4-chloro-2-chloromethyl-phenoxy)-1-[4-(4-fluoro-benzyl)-2R-methyl-piperazin-1-yl]-ethanone (0.223 mmol) in 1:1 ethanol:water (2 mL) was added sodium sulfite (0.75 g, 5.97 mmol). The reaction was heated to reflux for 12 hours. After cooling the reaction was concentrated in vacuo and purified by chromatography on silica gel to afford the title compound (example 2) as a sodium salt (10 mg).

EXAMPLE 3

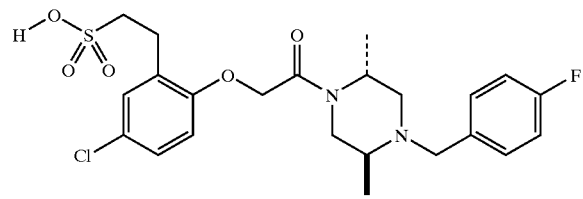

2-(5-Chloro-2-{2-[4-(4-fluoro-benzyl)-2R,5S-dimethyl-piperazin-1-yl]-2-oxo-ethoxy}-phenyl)-ethanesulfonic acid (5-Chloro-2-methoxy-phenyl)-methanol To a solution of 5-chloro-2-methoxy-benzoic acid methyl ester (20 g, 9.97 mmol) in THF (100 mL) at 0° C. was added dropwise a solution of lithium aluminum hydride (210 mL, 210 mmol, 1M soln. in THF). The solution was then warmed to reflux for 2 hours. The reaction was cooled to 0° C. and carefully quenched by the addition of cold water. The mixture was filtered through celite and the filter cake was washed with diethyl ether. The filtrate was washed with saturated aqueous sodium hydrogen carbonate then dried over magnesium sulfate. Concentration in vacuo gave the title compound (17.2 g).

(5-Chloro-2-methoxy-phenyl)-acetonitrile

To a solution of (5-chloro-2-methoxy-phenyl)-methanol (17.1 g, 99.1 mmol) in methylene chloride (100 mL) was added thionyl chloride (14.5 mL, 198 mmol). The reaction was stirred at reflux for 3 hours, cooled to room temperature and concentrated in vacuo. The crude product was dissolved in methylene chloride and washed with saturated aqueous sodium hydrogen carbonate then dried over magnesium sulfate. Concentration in vacuo gave 4-chloro-2-chloromethyl-1-methoxy-benzene (18.4 g). To a solution of 4-chloro-2-chloromethyl-1-methoxy-benzene (18.4 g, 96.4 mmol) in acetonitrile (100 mL) was added potassium cyanide (12.5 g, 193 mmol) and 18-crown-6 (2.54 g, 9.64 mmol). The reaction was stirred 12 hours at ambient temperature, diluted with ethyl acetate and washed with aqueous sodium hydrogen carbonate. The organic layer was dried over magnesium sulfate and concentrated in vacuo. The crude product was purified by passing it through a pad of silica gel, eluting with methylene chloride to give the title compound (17.2 g).

(5-Chloro-2-methoxy-phenyl)-acetic acid

To a solution of (5-chloro-2-methoxy-phenyl)-acetonitrile (17.2 g, 96.3 mmol) in ethanol (200 mL) and water (20 mL) was added potassium hydroxide (27 g, 481 mmol). The reaction was heated to reflux for 12 hours, cooled and the ethanol was removed by concentrating in vacuo. The remaining solution was acidified with aqueous hydrochloric acid (3 M) and extracted with diethyl ether. The organic layer was dried over magnesium sulfate and concentrated in vacuo to give the title compound (15.6 g).

(5-Chloro-2-hydroxy-phenyl)-acetic acid ethyl ester

A solution of (5-chloro-2-methoxy-phenyl)-acetic acid (15.5 g, 77.5 mmol) in 48% aqueous hydrogen bromide was heated to reflux for 20 hours. The solution was cooled, diluted with water and extracted with diethyl ether. The organic layer was dried over magnesium sulfate, filtered and concentrated in vacuo. The crude product was purified by trituration in 2:1 methylene chloride:hexanes to give (5-chloro-2-hydroxy-phenyl)-acetic acid (12.8 g). This was dissolved in a solution of ethanol saturated with hydrochloric acid and stirred 12 hours. The reaction was concentrated in vacuo, then the crude product was dissolved in diethyl ether and washed with saturated aqueous sodium hydrogen carbonate. The organic layer was dried over magnesium sulfate, filtered and concentrated in vacuo to give the title compound (12.7 g).

(5-Chloro-2-{2-[4-(4-fluoro-benzyl)-2,5-dimethyl-piperazin-1-yl]-2-oxo-ethoxy}-phenyl)-acetic acid ethyl ester To a solution of 2-chloro-1-[4-(4-fluoro-benzyl)-(2R,5S)-2,5-dimethyl-piperazin-1-yl]-ethanone (3.3 g, 11.0 mmol) in 2-butanone (100 mL) was added (5-chloro-2-hydroxy-phenyl)-acetic acid ethyl ester (2.3 g, 11.0 mmol), potassium carbonate (3.05 g, 22.1 mmol), and potassium iodide (1.83 g, 11.0 mmol). The reaction was heated at reflux for 48 hrs. The solution was cooled, diluted with ethyl acetate and washed with brine. The organic layer was dried over magnesium sulfate, filtered and concentrated in vacuo. The crude product was purified by dissolving in dichloromethane and passing through a pad of silica gel. Concentration in vacuo gave the title compound (5.13 g).

2-[4-Chloro-2-(2-hydroxy-ethyl)-phenoxy]-1-[4-(4-fluoro-benzyl)-2R,5S-dimethyl-piperazin-1-yl]-ethanone To a solution of (5-chloro-2-{2-[4-(4-fluoro-benzyl)-2,5-dimethyl-piperazin-1-yl]-2-oxo-ethoxy}-phenyl)-acetic acid ethyl ester (0.05 g, 0.1 mmol) in tert-butanol (1 ml) was added lithium borohydride (0.01 g, 0.26 mmol). The reaction was heated to reflux and methanol (0.2 ml) was added over one hour. After 1 hour the reaction was diluted with ethyl acetate. The organic layer was washed with brine, dried over magnesium sulfate, filtered and concentrated in vacuo and purified by silica gel chromatography to give the title compound (0.04 g).

2-(5-Chloro-2-{2-[4-(4-fluoro-benzyl)-2R,5S-dimethyl-piperazin-1-yl]-2-oxo-ethoxy}-phenyl)-ethanesulfonic acid To 2-[4-chloro-2-(2-hydroxy-ethyl)-phenoxy]-1-[4-(4-fluoro-benzyl)-2R,5S-dimethyl-piperazin-1-yl]-ethanone (0.072 g, 0.166 mmol) in methylene chloride (2 ml) was added thionyl chloride (0.1 ml, 0.83 mmol). The reaction was stirred at room temperature for 14 hours and heated to reflux for an additional 3 hours. After cooling the reaction was quenched by the addition of water and diluted with additional methylene chloride. The organic layer was washed with saturated sodium bicarbonate followed by saturated aqueous sodium chloride. The organic layer was then concentrated to afford the corresponding chloride as a brown oil (0.075 g).

To 2-[4-chloro-2-(2-chloro-ethyl)-phenoxy]-1-[4-(4-fluoro-benzyl)-2R,5S-dimethyl-piperazin-1-yl]-ethanone (0.075 g, 0.166 mmol) in 1:1 ethanol:water (5 mL) was added sodium sulfite (0.1 g, 0.79 mmol) and sodium iodide (0.024 g, 0.16 mmol). The reaction was heated to reflux for 20 hours. After cooling the reaction was concentrated and purified by chromatography on silica gel to afford the title compound (6.0 mg) as a sodium salt.

EXAMPLE 4

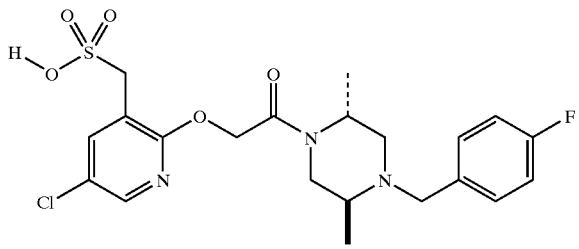

(5-Chloro-2-{2-[4-(4-fluoro-benzyl)-2R,5S-dimethyl-piperazin-1-yl]-2-oxo-ethoxy}-pyridin-3-yl)-methanesulfonic acid Acetic acid 2-[4-(4-fluoro-benzyl)-2R,5S-dimethyl-piperazin-1-yl]-2-oxo-ethyl ester To 1-(4-fluoro-benzyl)-2R,5S-dimethyl-piperazine (2 g, 9 mmol) in methylene chloride (45 ml) at 0° C. was added triethylamine (1.36 ml, 9.9 mmol) followed by acetic acid chlorocarbonylmethyl ester (1.06 ml, 9.9 mmol). After three hours the reaction was washed with saturated sodium bicarbonate. The organic layer was dried over magnesium sulfate, filtered, concentrated and purified by chromatography on silica gel to afford the title compound (2.6 g).

1-[4-(4-fluoro-benzyl)-(2R,5S)-2,5-dimethyl-piperazin-1-yl]-2-hydroxy-ethanone

To acetic acid 2-[4-(4-fluoro-benzyl)-2R,5S-dimethyl-piperazin-1-yl]-2-oxo-ethyl ester (2.6 g, 8 mmol) in tetrahydrofuran/methanol/water (2:2:1, 40 ml) was added lithium hydroxide hydrate (0.5 g, 12 mmol). After two hours the reaction was concentrated to dryness and taken up in ethyl acetate. The organic layer was washed with saturated sodium bicarbonate, dried over magnesium sulfate, filtered and concentrated to afford the title compound (2.12 g).

5-Chloro-2-{2-[4-(4-fluoro-benzyl)-2R,5S-dimethyl-piperazin-1-yl]-2-oxo-ethoxy}-nicotinic acid methyl ester To 1-[4-(4-fluoro-benzyl)-2R,5S-dimethyl-piperazin-1-yl]-2-hydroxy-ethanone (0.05 g, 0.178 mmol) in tetrahydrofuran (1 ml) at 0° C. was added sodium hydride (11 mg, 0.275 mmol) followed by 18-crown-6 (26 mg, 0.10 mmol). After 15 minutes the reaction was allowed to warm to ambient temperature and 2,5-dichloro-nicotinic acid methyl ester (55 mg, 0.267 mmol) (from modification of *J. Med. Chem.*, 1997, 40, 2674) in tetrahydrofuran (0.25 ml) was slowly added. After two hours the reaction was quenched with saturated aqueous sodium bicarbonate and extracted three times with ethyl acetate. The combined organic layers were washed with brine, dried over magnesium sulfate, filtered and concentrated in vacuo. Chromatography on silica gel gave the title compound (25 mg).

2-(5-Chloro-3-hydroxymethyl-pyridin-2-yloxy)-1-[4-(4-fluoro-benzyl)-2R,5S-dimethyl-piperazin-1-yl]-ethanone To 5-chloro-2-{2-[4-(4-fluoro-benzyl)-2R,5S-dimethyl-piperazin-1-yl]-2-oxo-ethoxy}-nicotinic acid methyl ester (24 mg, 0.053 mmol) and sodium borohydride (5 mg, 0.132 mmol) in tert-butanol (1 ml) at reflux was added methanol (0.04 ml, 1.06 mmol). After 90 minutes the reaction was cooled to ambient temperature and the solvent removed in vacuo. The reaction was taking up in water and extracted three times with methylene chloride. The combined organic layers were washed with brine, dried over magnesium sulfate, filtered and concentrated in vacuo. Chromatography on silica gel gave the title compound (22 mg).

(5-Chloro-2-{2-[4-(4-fluoro-benzyl)-2R,5S-dimethyl-piperazin-1-yl]-2-oxo-ethoxy}-pyridin-3-yl)-methanesulfonic acid To 2-(5-chloro-3-hydroxymethyl-pyridin-2-yloxy)-1-[4-(4-fluoro-benzyl)-2R,5S-dimethyl-piperazin-1-yl]-ethanone (0.067 g, 0.159 mmol) in methylene chloride (1.5 ml) was added thionyl chloride (0.04 ml, 0.49 mmol). The reaction was stirred at room temperature for one hour. The reaction was quenched by the addition of water and diluted with additional methylene chloride. The organic layer was washed with saturated aqueous sodium chloride and dried over magnesium sulfate. The organic layer was then concentrated to afford the corresponding chloride as a brown oil (0.07 g).

To 2-(5-chloro-3-chloromethyl-pyridin-2-yloxy)-1-[4-(4-fluoro-benzyl)-2R,5S-dimethyl-piperazin-1-yl]-ethanone (0.05 g, 0.161 mmol) in 1:1 ethanol:water (1 mL) was added sodium sulfite (0.07 g, 0.58 mmol). The reaction was heated to reflux for 20 hours. After cooling the reaction was concentrated and purified by chromatography on silica gel to afford the title compound (46 mg) as a sodium salt.

EXAMPLES 1–5

The compounds from Table 1 were prepared according to the methods described above.

| Example # | IUPAC | LRMS |
|---|---|---|
| 1 | (5-Chloro-2-{2-[4-(4-fluoro-benzyl)-2R,5S-dimethyl-piperazin-1-yl]-2-oxo-ethoxy}-phenyl)-methanesulfonic acid | 485.3 |
| 2 | (5-Chloro-2-{2-[4-(4-fluoro-benzyl)-2R-methyl-piperazin-1-yl]-2-oxo-ethoxy}-phenyl)-methane-sulfonic acid | 469.1 |
| 3 | 2-(5-Chloro-2-{2-[4-(4-fluoro-benzyl)-2R,5S-dimethyl-piperazin-1-yl]-2-oxo-ethoxy}-phenyl)-ethanesulfonic acid | 499.4 |
| 4 | (5-Chloro-2-{2-[4-(4-fluoro-benzyl)-2R,5S-dimethyl-piperazin-1-yl]-2-oxo-ethoxy}-pyridin-3-yl)-methanesulfonic acid | 486.4 |
| 5 | (5-Bromo-2-{2-[4-(4-fluoro-benzyl)-2R,5S-dimethyl-piperazin-1-yl]-2-oxo-ethoxy}-phenyl)-methanesulfonic acid | 529.1 |

-continued

| Example # | IUPAC | LRMS |
|---|---|---|
| 6 | (5-Bromo-2-{2-[4-(4-fluoro-benzyl)-2R-methyl-piperazin-1-yl]-2-ethoxy}-phenyl)-methane-sulfonic acid | 513.2 |

What is claimed is:

1. A compound of the formula

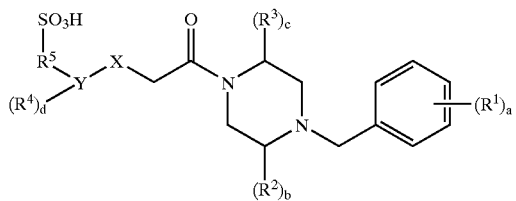

I or the pharmaceutically acceptable salts thereof; wherein
a=0–5,
b=0–2,
c=0–2
d=0–4
X is —O—, —S—, —CH$_2$—, —NR$^6$—
Y is (C$_6$–C$_{10}$)aryl, or (C$_2$–C$_9$)heteroaryl,
each R$^1$ is independently selected from the group consisting of: H—, HO—, halo-, (C$_1$–C$_8$)alkyl-optionally substituted with 1–3 fluorine atoms, (C$_1$–C$_8$)alkyl-O— wherein the alkyl group is optionally substituted with 1–3 fluorine atoms, HO—(C$_1$–C$_8$)alkyl-, NC—, H$_2$N—, H$_2$N—(C$_1$–C$_8$)alkyl-, HO—(C=O)—, (C$_1$–C$_8$)alkyl-(C=O)—, (C$_1$–C$_8$)alkyl-(C=O)—(C$_1$–C$_8$)alkyl-, H$_2$N—(C=O)—, H$_2$N—(C=O)—(C$_1$–C$_8$)alkyl-;
each R$^2$ and R$^3$ is independently selected from the group consisting of: H—, oxo, (C$_1$–C$_8$)alkyl- substituted with 1–3 fluorine atoms, (C$_1$–C$_8$)alkyl-, (C$_3$–C$_8$)cycloalkyl-, (C$_3$–C$_8$)cycloalkyl-(C$_1$–C$_8$)alkyl-, (C$_6$–C$_{10}$)aryl-, (C$_6$–C$_{10}$)aryl-(C$_1$–C$_8$)alkyl-, HO—(C$_1$–C$_8$)alkyl-, (C$_1$–C$_8$)alkyl-O—(C$_1$–C$_8$)alkyl-, H$_2$N—(C$_1$–C$_8$)alkyl-, (C$_1$–C$_8$)alkyl-NH—(C$_1$–C$_8$)alkyl-, [(C$_1$–C$_8$)alkyl]$_2$N—(C$_1$–C$_8$)alkyl-, (C$_2$–C$_9$)heterocyclyl-(C$_1$–C$_8$)alkyl-, (C$_1$–C$_8$)alkyl-(C=O)—NH—(C$_1$–C$_8$)alkyl-, (C$_1$–C$_8$)alkyl-O—(C=O)—NH—(C$_1$–C$_8$)alkyl-, H$_2$N—(C=O)—NH—(C$_1$–C$_8$)alkyl-, (C$_1$–C$_8$)alkyl-SO$_2$—NH—(C$_1$–C$_8$)alkyl-, (C$_2$–C$_9$)heteroaryl-(C$_1$–C$_8$)alkyl-, H$_2$N—(C=O)—, H$_2$N—(C=O)—(C$_1$–C$_8$)alkyl-;
each R$^4$ is independently selected from the group consisting of: H—, HO—, halo-, NC—, HO—(C=O)—, H$_2$N—, (C$_1$–C$_8$)alkyl-NH—, [(C$_1$–C$_8$)alkyl]$_2$N—, (C$_1$–C$_8$)alkyl-optionally substituted with 1–3 fluorine atoms, (C$_1$–C$_8$)alkyl-O— wherein the alkyl group is optionally substituted with 1–3 fluorine atoms, HO—(C$_1$–C$_8$)alkyl-, (C$_1$–C$_8$)alkyl-O—(C$_1$–C$_8$)alkyl-, H$_2$N—(C$_1$–C$_8$)alkyl-, (C$_1$–C$_8$)alkyl-NH—(C$_1$–C$_8$)alkyl-, [(C$_1$–C$_8$)alkyl]$_2$N—(C$_1$–C$_8$)alkyl-, (C$_1$–C$_8$)alkyl-(C=O)—, (C$_1$–C$_8$)alkyl-(C=O)—(C$_1$–C$_8$)alkyl-, (C$_6$–C$_{10}$)aryl-, (C$_2$–C$_9$)heteroaryl-, (C$_6$–C$_{10}$)aryloxy-, H$_2$N—(C=O)—, H$_2$N—(C=O)—(C$_1$–C$_8$)alkyl-, (C$_1$–C$_8$)alkyl-NH—(C=O)—, (C$_1$–C$_8$)alkyl-NH—(C=O)—(C$_1$–C$_8$)alkyl-, [(C$_1$–C$_8$)alkyl]$_2$N—(C=O)—, [(C$_1$–C$_8$)alkyl]$_2$—N—(C=O)—(C$_1$–C$_8$)alkyl-, (C$_3$–C$_8$)cycloalkyl-, (C$_1$–C$_8$)alkyl-SO$_2$—, NC—(C$_1$–C$_8$)alkyl-, (C$_1$–C$_8$)alkyl-(C=O)—NH—, H$_2$N—(C=O)—NH—, H$_2$N—(C=O)—NH—(C$_1$–C$_8$)alkyl-;
R$^5$ is (C$_1$–C$_8$)alkyl-.

2. A compound according to claim 1, wherein R$^1$ is selected from the group consisting of: H—, HO—, halo, NC—, (C$_1$–C$_8$)alkyl optionally substituted with 1–3 fluorine atoms and (C$_1$–C$_8$)alkyl-O— wherein the alkyl group is optionally substituted with 1–3 fluorine atoms.

3. A compound according to claim 1, wherein R$^2$ and R$^3$ are each independently selected from the group consisting of: H—, (C$_1$–C$_8$)alkyl-, (C$_3$–C$_8$)cycloalkyl-, (C$_3$–C$_8$)cycloalkyl-(C$_3$–C$_8$)alkyl-, (C$_6$–C$_{10}$)aryl-, (C$_6$–C$_{10}$)aryl-(C$_1$–C$_8$)alkyl-, HO—(C$_1$–C$_8$)alkyl-, H$_2$N—(C$_1$–C$_8$)alkyl-, (C$_2$–C$_9$)heterocyclyl-(C$_1$–C$_8$)alkyl-, (C$_1$–C$_8$)alkyl-O—(C=O)—NH—(C$_1$–C$_8$)alkyl-, H$_2$N—(C=O)—NH—(C$_1$–C$_8$)alkyl-, (C$_1$–C$_8$)alkyl-SO$_2$—NH—(C$_1$–C$_8$)alkyl-, (C$_2$–C$_9$)heteroaryl-(C$_1$–C$_8$)alkyl-, H$_2$N—(C=O)—, H$_2$N—(C=O)—(C$_1$–C$_8$)alkyl-.

4. A compound according to claim 1, wherein X is —CH$_2$— and Y is (C$_6$–C$_{10}$)aryl.

5. A compound according to claim 1, wherein X is —CH$_2$— and Y is (C$_2$–C$_9$)heteroaryl.

6. A compound according to claim 1, wherein R$^4$ is selected from the group consisting of H—, HO—, NC—, (C$_1$–C$_8$)alkyl-optionally substituted with 1–3 fluorine atoms, (C$_1$–C$_8$)alkyl-O— wherein the alkyl group is optionally substituted with 1–3 fluorine atoms, (C$_1$–C$_8$)alkyl-(C=O)—, and halo.

7. A compound according to claim 2 wherein R$^2$ and R$^3$ are each independently selected from the group consisting of: H—, (C$_1$–C$_8$)alkyl-, (C$_3$–C$_8$)cycloalkyl-, (C$_3$–C$_8$)cycloalkyl-(C$_1$–C$_8$)alkyl-, (C$_6$–C$_{10}$)aryl-, (C$_6$–C$_{10}$)aryl-(C$_1$–C$_8$)alkyl-, HO—(C$_1$–C$_8$)alkyl-, H$_2$N—(C$_1$–C$_8$)alkyl-, (C$_2$–C$_9$)heterocyclyl-(C$_1$–C$_8$)alkyl-, (C$_1$–C$_8$)alkyl-O—(C=O)—NH—(C$_1$–C$_8$)alkyl-, H$_2$N—(C=O)—NH—(C$_1$–C$_8$)alkyl-, (C$_1$–C$_8$)alkyl-SO$_2$—NH—(C$_1$–C$_8$)alkyl-, (C$_2$–C$_9$)heteroaryl-(C$_1$–C$_8$)alkyl-, H$_2$N—(C=O)—, H$_2$N—(C=O)—(C$_1$–C$_8$)alkyl-.

8. A compound according to claim 7 wherein X is —CH$_2$— and Y is (C$_6$–C$_{10}$)aryl.

9. A compound according to claim 7 wherein X is —CH$_2$— and Y is (C$_2$–C$_9$)heteroaryl.

10. A compound according to claim 7 wherein R$^4$ is selected from the group consisting of: H—, HO—, NC—, (C$_1$–C$_8$)alkyl-optionally substituted with 1–3 fluorine atoms, (C$_1$–C$_8$)alkyl-O— wherein the alkyl group is optionally substituted with 1–3 fluorine atoms, (C$_1$–C$_8$)alkyl-(C=O)—, and halo.

11. A compound according to claim 8 wherein R$^4$ is selected from the group consisting of: H—, HO—, NC—, (C$_1$–C$_8$)alkyl-optionally substituted with 1–3 fluorine atoms, (C$_1$–C$_8$)alkyl-O— wherein the alkyl group is optionally substituted with 1–3 fluorine atoms, (C$_1$–C$_8$)alkyl-(C=O)—, and halo.

12. A compound according to claim 9 wherein R$^4$ is selected from the group consisting of: H—, HO—, NC—, (C$_1$–C$_8$)alkyl-optionally substituted with 1–3 fluorine atoms, (C$_1$–C$_8$)alkyl-O— wherein the alkyl group is optionally substituted with 1–3 fluorine atoms, (C$_1$–C$_8$)alkyl-(C=O)—, and halo.

13. A compound according to claim 2 wherein R$^2$ and R$^3$ are each independently selected from the group consisting of: H—, (C$_1$–C$_8$)alkyl- and (C$_3$–C$_8$)cycloalkyl-.

14. A compound according to claim 13 wherein R$^4$ is selected from the group consisting of: H—, HO—, NC—, ($C_1$–$C_8$)alkyl-optionally substituted with 1–3 fluorine atoms, ($C_1$–$C_8$)alkyl-O— wherein the alkyl group is optionally substituted with 1–3 fluorine atoms, ($C_1$–$C_8$)alkyl-(C=O)—, and halo.

15. A compound according to claim 14 wherein X is —$CH_2$— and Y is ($C_6$–$C_{10}$)aryl.

16. A compound according to claim 14 wherein X is —$CH_2$— and Y is ($C_2$–$C_9$)heteroaryl.

17. A compound according to claim 15 wherein $R^5$ is $C_1$ to $C_3$ alkyl.

18. A compound according to claim 16 wherein $R^5$ is $C_1$ to $C_3$ alkyl.

19. A compound selected from the list consisting of:
  2-(5-Chloro-2-{2-[4-(4-fluoro-benzyl)-2R,5S-dimethyl-piperazin-1-yl]-2-oxo-ethylamino}-phenyl)-ethanesulfonic acid; and
  (5-Chloro-2-{2-[4-(4-fluoro-benzyl)-2R,5S-dimethyl-piperazin-1-yl]-2-oxo-ethylamino}-phenyl)-methanesulfonic acid, or a pharmaceutically acceptable salt thereof.

20. A pharmaceutical composition for treating or preventing a disorder or condition selected from autoimmune diseases, lupus, acute and chronic inflammatory conditions, allergic conditions, infection associated with inflammation, viral, chronic bronchitis, xeno-transplantation, transplantation tissue rejection, atherosclerosis, restenosis, HIV infectivity, and granulomatous in a mammal, comprising an amount of a compound according to claim 1, or a pharmaceutically acceptable salt thereof, that is effective in treating or preventing such disorder or condition and a pharmaceutically acceptable carrier.

21. A pharmaceutical composition for treating or preventing a disorder or condition that can be treated or prevented by inhibiting MIP-1α and/or RANTES binding to the receptor CCR1 in a mammal, comprising an amount of a compound according to claim 1, or a pharmaceutically acceptable salt thereof, effective in treating or preventing such disorder or condition and a pharmaceutically acceptable carrier.

22. A method for treating or preventing a disorder or condition selected from autoimmune diseases, lupus, acute and chronic inflammatory conditions, allergic conditions, infection associated with inflammation, viral, chronic bronchitis, xeno-transplantation, transplantation tissue rejection, atherosclerosis, restenosis, HIV infectivity, and granulomatous in a mammal, comprising administering to a mammal in need of such treatment or prevention an amount of a compound according to claim 1, or a pharmaceutically acceptable salt thereof, that is effective in treating or preventing such disorder or condition.

23. A method for treating or preventing a disorder or condition that can be treated or prevented by antagonizing the CCR1 receptor in a mammal, comprising administering to a mammal in need of such treatment or prevention an amount of a compound according to claim 1, or a pharmaceutically acceptable salt thereof, that is effective in treating or preventing such disorder or condition.

24. A pharmaceutical composition for treating or preventing a disorder or condition that can be treated or prevented by antagonizing the CCR1 receptor in a mammal selected from autoimmune diseases, lupus, acute and chronic inflammatory conditions, allergic conditions, infection associated with inflammation, viral, chronic bronchitis, xeno-transplantation, transplantation tissue rejection, atherosclerosis, restenosis, HIV infectivity, and granulomatous in a mammal, comprising a CCR1 receptor antagonizing effective amount of a compound according to claim 1, or a pharmaceutically acceptable salt thereof, and a pharmaceutically acceptable carrier.

25. A pharmaceutical composition for treating or preventing a disorder or condition that can be treated or prevented by antagonizing the CCR1 receptor in a mammal, comprising a CCR1 receptor antagonizing effective amount of a compound according to claim 1, or a pharmaceutically acceptable salt thereof, and a pharmaceutically acceptable carrier.

26. A compound of the formula

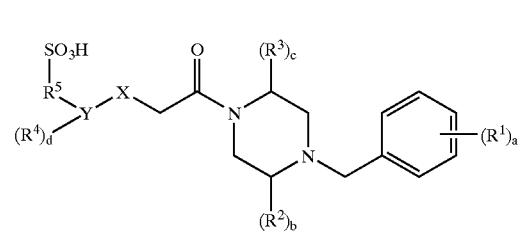

or the pharmaceutically acceptable salts thereof; wherein
  a=0–5,
  b=0–2,
  c=0–2
  d=0–4
  X is —O—
  Y is ($C_6$–$C_{10}$)aryl, or ($C_2$–$C_9$)heteroaryl,
  each $R^1$ is independently selected from the group consisting of: H—, HO—, halo-, ($C_1$–$C_8$)alkyl-optionally substituted with 1–3 fluorine atoms, ($C_1$–$C_8$)alkyl-O— wherein the alkyl group is optionally substituted with 1–3 fluorine atoms, HO—($C_1$–$C_8$)alkyl-, NC—, $H_2N$—, $H_2N$—($C_1$–$C_8$)alkyl-, HO—(C=O)—, ($C_1$–$C_8$)alkyl-(C=O)—, ($C_1$–$C_8$)alkyl-(C=O)—($C_1$–$C_8$)alkyl-, $H_2N$—(C=O)—, $H_2N$—(C=O)—($C_1$–$C_8$)alkyl-;
  each $R^2$ and $R^3$ is independently selected from the group consisting of: H—, oxo, ($C_1$–$C_8$)alkyl- substituted with 1–3 fluorine atoms, ($C_1$–$C_8$)alkyl-, ($C_3$–$C_8$)cycloalkyl-, ($C_3$–$C_8$)cycloalkyl-($C_1$–$C_8$)alkyl-, ($C_6$–$C_{10}$)aryl-, ($C_6$–$C_{10}$)aryl-($C_1$–$C_8$)alkyl-, HO—($C_1$–$C_8$)alkyl-, ($C_1$–$C_8$)alkyl-O—($C_1$–$C_8$)alkyl-, $H_2N$—($C_1$–$C_8$)alkyl-, ($C_1$–$C_8$)alkyl-NH—($C_1$–$C_8$)alkyl-, [($C_1$–$C_8$)alkyl]$_2$N—($C_1$–$C_8$)alkyl-, ($C_2$–$C_9$)heterocyclyl-($C_1$–$C_8$)alkyl-, ($C_1$–$C_8$)alkyl-(C=O)—NH—($C_1$–$C_8$)alkyl-, ($C_1$–$C_8$)alkyl-O—(C=O)—NH—($C_1$–$C_8$)alkyl-, $H_2N$—(C=O)—NH—($C_1$–$C_8$)alkyl-, ($C_1$–$C_8$)alkyl-$SO_2$—NH—($C_1$–$C_8$)alkyl-, ($C_2$–$C_9$)heteroaryl-($C_1$–$C_8$)alkyl-, $H_2N$—(C=O)—, $H_2N$—(C=O)—($C_1$–$C_8$)alkyl-;
  each $R^4$ is independently selected from the group consisting of: H—, HO—, halo-, NC—, HO—(C=O)—, $H_2N$—, ($C_1$–$C_8$)alkyl-NH—, [($C_1$–$C_8$)alkyl]$_2$N—, ($C_1$–$C_8$)alkyl-optionally substituted with 1–3 fluorine atoms, ($C_1$–$C_8$)alkyl-O— wherein the alkyl group is optionally substituted with 1–3 fluorine atoms, HO—($C_1$–$C_8$)alkyl-, ($C_1$–$C_8$)alkyl-O—($C_1$–$C_8$)alkyl-, $H_2N$—($C_1$–$C_8$)alkyl-, ($C_1$–$C_8$)alkyl-NH—($C_1$–$C_8$)alkyl-, [($C_1$–$C_8$)alkyl]$_2$N—($C_1$–$C_8$)alkyl-, ($C_1$–$C_8$)alkyl-(C=O)—, ($C_1$–$C_8$)alkyl-(C=O)—($C_1$–$C_8$)alkyl-, ($C_6$–$C_{10}$)aryl-, ($C_2$–$C_9$)heteroaryl-, ($C_6$–$C_{10}$)aryloxy-, $H_2N$—(C=O)—, $H_2N$—(C=O)—($C_1$–$C_8$)alkyl-, ($C_1$–$C_8$)alkyl-NH—(C=O)—, ($C_1$–$C_8$)alkyl-NH—(C=O)—($C_1$–$C_8$)alkyl-, [($C_1$–$C_8$)alkyl]$_2$N—

(C=O)—, [(C$_1$–C$_8$)alkyl]$_2$—N—(C=O)—(C$_1$–C$_8$) alkyl-, (C$_3$–C$_8$)cycloalkyl-, (C$_1$–C$_8$)alkyl-SO$_2$—, NC—(C$_1$–C$_8$)alkyl-, (C$_1$–C$_8$)alkyl-(C=O)—NH—, H$_2$N—(C=O)—NH—, H$_2$N—(C=O)—NH—(C$_1$–C$_8$)alkyl-;

R$^5$ is (C$_1$–C$_8$)alkyl-.

27. A compound according to claim 26, wherein R$^1$ is selected from the group consisting of: H—, HO—, halo, NC—, (C$_1$–C$_8$)alkyl optionally substituted with 1–3 fluorine atoms and (C$_1$–C$_8$)alkyl-O— wherein the alkyl group is optionally substituted with 1–3 fluorine atoms.

28. A compound according to claim 26, wherein R$^2$ and R$^3$ are each independently selected from the group consisting of: H—, (C$_1$–C$_8$)alkyl-, (C$_3$–C$_8$)cycloalkyl-, (C$_3$–C$_8$)cycloalkyl-(C$_3$–C$_8$)alkyl-, (C$_6$–C$_{10}$)aryl-, (C$_6$–C$_{10}$)aryl-(C$_1$–C$_8$)alkyl-, HO—(C$_1$–C$_8$)alkyl-, H$_2$N—(C$_1$–C$_8$)alkyl-, (C$_2$–C$_9$)heterocyclyl-(C$_1$–C$_8$)alkyl-, (C$_1$–C$_8$)alkyl-O—(C=O)—NH—(C$_1$–C$_8$)alkyl-, H$_2$N—(C=O)—NH—(C$_1$–C$_8$)alkyl-, (C$_1$–C$_8$)alkyl-SO$_2$—NH—(C$_1$–C$_8$)alkyl-, (C$_2$–C$_9$)heteroaryl-(C$_1$–C$_8$)alkyl-, H$_2$N—(C=O)—, H$_2$N—(C=O)—(C$_1$–C$_8$)alkyl-.

29. A compound according to claim 26, wherein Y is (C$_6$–C$_{10}$)aryl.

30. A compound according to claim 26, wherein Y is (C$_2$–C$_9$)heteroaryl.

31. A compound according to claim 26, wherein R$^4$ is selected from the group consisting of H—, HO—, NC—, (C$_1$–C$_8$)alkyl-optionally substituted with 1–3 fluorine atoms, (C$_1$–C$_8$)alkyl-O— wherein the alkyl group is optionally substituted with 1–3 fluorine atoms, (C$_1$–C$_8$)alkyl-(C=O)—, and halo.

32. A compound according to claim 27 wherein R$^2$ and R$^3$ are each independently selected from the group consisting of: H—, (C$_1$–C$_8$)alkyl-, (C$_3$–C$_8$)cycloalkyl-, (C$_3$–C$_8$)cycloalkyl-(C$_1$–C$_8$)alkyl-, (C$_6$–C$_{10}$)aryl-, (C$_6$–C$_{10}$)aryl-(C$_1$–C$_8$)alkyl-, HO—(C$_1$–C$_8$)alkyl-, H$_2$N—(C$_1$–C$_8$)alkyl-, (C$_2$–C$_9$)heterocyclyl-(C$_1$–C$_8$)alkyl-, (C$_1$–C$_8$)alkyl-O—(C=O)—NH—(C$_1$–C$_8$)alkyl-, H$_2$N—(C=O)—NH—(C$_1$–C$_8$)alkyl-, (C$_1$–C$_8$)alkyl-SO$_2$—NH—(C$_1$–C$_8$)alkyl-, (C$_2$–C$_9$)heteroaryl-(C$_1$–C$_8$)alkyl-, H$_2$N—(C=O)—, H$_2$N—(C=O)—(C$_1$–C$_8$)alkyl-.

33. A compound according to claim 32 wherein Y is (C$_6$–C$_{10}$)aryl.

34. A compound according to claim 32 wherein Y is (C$_2$–C$_9$)heteroaryl.

35. A compound according to claim 32 wherein R$^4$ is selected from the group consisting of: H—, HO—, NC—, (C$_1$–C$_8$)alkyl-optionally substituted with 1–3 fluorine atoms, (C$_1$–C$_8$)alkyl-O— wherein the alkyl group is optionally substituted with 1–3 fluorine atoms, (C$_1$–C$_8$)alkyl-(C=O)—, and halo.

36. A compound according to claim 33 wherein R$^4$ is selected from the group consisting of: H—, HO—, NC—, (C$_1$–C$_8$)alkyl-optionally substituted with 1–3 fluorine atoms, (C$_1$–C$_8$)alkyl-O— wherein the alkyl group is optionally substituted with 1–3 fluorine atoms, (C$_1$–C$_8$)alkyl-(C=O)—, and halo.

37. A compound according to claim 34 wherein R$^4$ is selected from the group consisting of: H—, HO—, NC—, (C$_1$–C$_8$)alkyl-optionally substituted with 1–3 fluorine atoms, (C$_1$–C$_8$)alkyl-O— wherein the alkyl group is optionally substituted with 1–3 fluorine atoms, (C$_1$–C$_8$)alkyl-(C=O)—, and halo.

38. A compound according to claim 27 wherein R$^2$ and R$^3$ are each independently selected from the group consisting of: H—, (C$_1$–C$_8$)alkyl- and (C$_3$–C$_8$)cycloalkyl-.

39. A compound according to claim 38 wherein R$^4$ is selected from the group consisting of: H—, HO—, NC—, (C$_1$–C$_8$)alkyl-optionally substituted with 1–3 fluorine atoms, (C$_1$–C$_8$)alkyl-O— wherein the alkyl group is optionally substituted with 1–3 fluorine atoms, (C$_1$–C$_8$)alkyl-(C=O)—, and halo.

40. A compound according to claim 39 wherein Y is (C$_6$–C$_{10}$)aryl.

41. A compound according to claim 39 wherein Y is (C$_2$–C$_9$)heteroaryl.

42. A compound according to claim 40 wherein R$^5$ is C$_1$ to C$_3$ alkyl.

43. A compound according to claim 41 wherein R$^5$ is C$_1$ to C$_3$ alkyl.

44. A compound selected from the list consisting of:

(5-Bromo-2-{2-[4-(4-fluoro-benzyl)-2R-methyl-piperazin-1-yl]-2-oxo-ethoxy}-phenyl)-methanesulfonic acid;

(5-Chloro-2-{2-[4-(4-chloro-benzyl)-2R,5S-dimethyl-piperazin-1-yl]-2-oxo-ethoxy}-phenyl)-methanesulfonic acid;

2-(5-Bromo-2-{2-[4-(4-fluoro-benzyl)-2R-methyl-piperazin-1-yl]-2-oxo-ethoxy}-phenyl)-ethanesulfonic acid;

2-(5-Chloro-2-{2-[4-(4-chloro-benzyl)-2R,5S-dimethyl-piperazin-1-yl]-2-oxo-ethoxy}-phenyl)-ethanesulfonic acid;

(4-Bromo-2-{2-[4-(4-fluoro-benzyl)-2R,5S-dimethyl-piperazin-1-yl]-2-oxo-ethoxy}-phenyl)-methanesulfonic acid;

(3-Chloro-2-{2-[4-(4-fluoro-benzyl)-2R,5S-dimethyl-piperazin-1-yl]-2-oxo-ethoxy}-phenyl)-methanesulfonic acid;

(5-Bromo-2-{2-[4-(4-chloro-benzyl)-2R,5S-dimethyl-piperazin-1-yl]-2-oxo-ethoxy}-phenyl)-methanesulfonic acid;

(5-Chloro-2-{2-[4-(4-fluoro-benzyl)-2R-methyl-piperazin-1-yl]-2-oxo-ethoxy}-pyridin-3-yl)-methanesulfonic acid;

(5-Bromo-2-{2-[4-(4-fluoro-benzyl)-2R-methyl-piperazin-1-yl]-2-oxo-ethoxy}-pyridin-3-yl)-methanesulfonic acid;

(5-Chloro-2-{2-[4-(3,4-difluoro-benzyl)-2R,5S-dimethyl-piperazin-1-yl]-2-oxo-ethoxy}-phenyl)-methanesulfonic acid;

(5-Bromo-2-{2-[4-(3,4-difluoro-benzyl)-2R,5S-dimethyl-piperazin-1-yl]-2-oxo-ethoxy}-phenyl)-methanesulfonic acid;

(5-Chloro-2-{2-[4-(4-chloro-benzyl)-2R-methyl-piperazin-1-yl]-2-oxo-ethoxy}-phenyl)-methanesulfonic acid;

(5-Bromo-2-{2-[4-(4-chloro-benzyl)-2R-methyl-piperazin-1-yl]-2-oxo-ethoxy}-phenyl)-methanesulfonic acid;

(5-Chloro-2-{2-[4-(3,4-difluoro-benzyl)-2R-methyl-piperazin-1-yl]-2-oxo-ethoxy}-phenyl)-methanesulfonic acid;

(5-Bromo-2-{2-[4-(3,4-difluoro-benzyl)-2R-methyl-piperazin-1-yl]-2-oxo-ethoxy}-phenyl)-methanesulfonic acid;

2-(5-Chloro-2-{2-[4-(4-fluoro-benzyl)-2R,5S-dimethyl-piperazin-1-yl]-2-oxo-ethoxy}-phenyl)-ethanesulfonic acid;

(5-Bromo-2-{2-[4-(4-fluoro-benzyl)-2R-methyl-piperazin-1-yl]-2-oxo-ethoxy}-pyridin-3-yl)-ethanesulfonic acid;

(4-Chloro-2-{2-[4-(4-fluoro-benzyl)-2R,5S-dimethyl-piperazin-1-yl]-2-oxo-ethoxy}-phenyl)-methanesulfonic acid;

(3-Bromo-2-{2-[4-(4-fluoro-benzyl)-2R,5S-dimethyl-piperazin-1-yl]-2-oxo-ethoxy}-phenyl)-methanesulfonic acid;

(2-Chloro-6-{2-[4-(4-fluoro-benzyl)-2R,5S-dimethyl-piperazin-1-yl]-2-oxo-ethoxy}-phenyl)-methanesulfonic acid;

(5-Bromo-2-{2-[2R-ethyl-4-(4-fluoro-benzyl)-5S-methyl-piperazin-1-yl]-2-oxo-ethoxy}-phenyl)-methanesulfonic acid;

2-(5-Bromo-2-{2-[4-(4-fluoro-benzyl)-2R,5S-dimethyl-piperazin-1-yl]-2-oxo-ethoxy}-phenyl)-ethanesulfonic acid;

(5-Chloro-2-{2-[4-(4-fluoro-benzyl)-2R-methyl-piperazin-1-yl]-2-oxo-ethoxy}-phenyl)-methanesulfonic acid;

2-(5-Bromo-2-{2-[4-(4-chloro-benzyl)-2R,5S-dimethyl-piperazin-1-yl]-2-oxo-ethoxy}-phenyl)-ethanesulfonic acid;

2-(5-Chloro-2-{2-[4-(3,4-difluoro-benzyl)-2R,5S-dimethyl-piperazin-1-yl]-2-oxo-ethoxy}-phenyl)-ethanesulfonic acid;

2-(5-Chloro-2-{2-[4-(4-chloro-benzyl)-2R-methyl-piperazin-1-yl]-2-oxo-ethoxy}-phenyl)-ethanesulfonic acid;

2-(5-Bromo-2-{2-[4-(4-chloro-benzyl)-2R-methyl-piperazin-1-yl]-2-oxo-ethoxy}-phenyl)-ethanesulfonic acid;

(5-Chloro-2-{2-[4-(4-fluoro-benzyl)-2R,5S-dimethyl-piperazin-1-yl]-2-oxo-ethoxy}-phenyl)-methanesulfonic acid;

2-(5-Chloro-2-{2-[4-(3,4-difluoro-benzyl)-2R-methyl-piperazin-1-yl]-2-oxo-ethoxy}-phenyl)-ethanesulfonic acid;

(5-Bromo-2-{2-[4-(4-chloro-benzyl)-2R-methyl-piperazin-1-yl]-2-oxo-ethoxy}-pyridin-3-yl)-ethanesulfonic acid;

3-(5-Bromo-2-{2-[4-(4-fluoro-benzyl)-2R,5S-dimethyl-piperazin-1-yl]-2-oxo-ethoxy}-phenyl)-propane-1-sulfonic acid;

3-(5-Chloro-2-{2-[4-(4-fluoro-benzyl)-2R-methyl-piperazin-1-yl]-2-oxo-ethoxy}-phenyl)-propane-1-sulfonic acid;

3-(5-Bromo-2-{2-[4-(4-fluoro-benzyl)-2R-methyl-piperazin-1-yl]-2-oxo-ethoxy}-phenyl)-propane-1-sulfonic acid;

(2-Bromo-6-{2-[4-(4-fluoro-benzyl)-2R,5S-dimethyl-piperazin-1-yl]-2-oxo-ethoxy}-phenyl)-methanesulfonic acid;

(5-Chloro-2-{2-[2R-ethyl-4-(4-fluoro-benzyl)-5S-methyl-piperazin-1-yl]-2-oxo-ethoxy}-phenyl)-methanesulfonic acid;

3-(5-Chloro-2-{2-[4-(4-chloro-benzyl)-2R,5S-dimethyl-piperazin-1-yl]-2-oxo-ethoxy}-phenyl)-propane-1-sulfonic acid;

2-(5-Chloro-2-{2-[4-(4-fluoro-benzyl)-2R-methyl-piperazin-1-yl]-2-oxo-ethoxy}-phenyl)-ethanesulfonic acid;

3-(5-Bromo-2-{2-[4-(4-chloro-benzyl)-2R,5S-dimethyl-piperazin-1-yl]-2-oxo-ethoxy}-phenyl)-propane-1-sulfonic acid;

2-(5-Bromo-2-{2-[4-(3,4-difluoro-benzyl)-2R,5S-dimethyl-piperazin-1-yl]-2-oxo-ethoxy}-phenyl)-ethanesulfonic acid;

3-(5-Chloro-2-{2-[4-(3,4-difluoro-benzyl)-2R,5S-dimethyl-piperazin-1-yl]-2-oxo-ethoxy}-phenyl)-propane-1-sulfonic acid;

3-(5-Chloro-2-{2-[4-(4-fluoro-benzyl)-2R,5S-dimethyl-piperazin-1-yl]-2-oxo-ethoxy}-pyridin-3-yl)-propane-1-sulfonic acid;

(5-Bromo-2-{2-[4-(4-fluoro-benzyl)-2R,5S-dimethyl-piperazin-1-yl]-2-oxo-ethoxy}-pyridin-3-yl)-methanesulfonic acid;

3-(5-Chloro-2-{2-[4-(4-chloro-benzyl)-2R-methyl-piperazin-1-yl]-2-oxo-ethoxy}-phenyl)-propane-1-sulfonic acid;

(5-Bromo-2-{2-[4-(3,4-difluoro-benzyl)-2R-methyl-piperazin-1-yl]-2-oxo-ethoxy}-pyridin-3-yl)-ethanesulfonic acid;

(5-Bromo-2-{2-[2R-ethyl-4-(4-fluoro-benzyl)-5S-methyl-piperazin-1-yl]-2-oxo-ethoxy}-phenyl)-ethanesulfonic acid;

3-(5-Bromo-2-{2-[4-(4-chloro-benzyl)-2R-methyl-piperazin-1-yl]-2-oxo-ethoxy}-phenyl)-propane-1-sulfonic acid;

3-(5-Chloro-2-{2-[4-(3,4-difluoro-benzyl)-2R-methyl-piperazin-1-yl]-2-oxo-ethoxy}-phenyl)-propane-1-sulfonic acid;

(5-Bromo-2-{2-[4-(4-fluoro-benzyl)-2R,5S-dimethyl-piperazin-1-yl]-2-oxo-ethoxy}-pyridin-3-yl)-ethanesulfonic acid;

3-(5-Bromo-2-{2-[4-(3,4-difluoro-benzyl)-2R-methyl-piperazin-1-yl]-2-oxo-ethoxy}-phenyl)-propane-1-sulfonic acid;

(2-{2-[4-(4-Fluoro-benzyl)-2R,5S-dimethyl-piperazin-1-yl]-2-oxo-ethoxy}-5-methyl-phenyl)-methanesulfonic acid;

2-(5-Bromo-2-{2-[4-(3,4-difluoro-benzyl)-2R-methyl-piperazin-1-yl]-2-oxo-ethoxy}-phenyl)-ethanesulfonic acid;

3-(5-Chloro-2-{2-[4-(4-fluoro-benzyl)-2R,5S-dimethyl-piperazin-1-yl]-2-oxo-ethoxy}-phenyl)-propane-1-sulfonic acid;

(5-Chloro-2-{2-[4-(4-fluoro-benzyl)-2R,5S-dimethyl-piperazin-1-yl]-2-oxo-ethoxy}-pyridin-3-yl)-methanesulfonic acid;

(5-Bromo-2-{2-[4-(4-fluoro-benzyl)-2R,5S-dimethyl-piperazin-1-yl]-2-oxo-ethoxy}-phenyl)-methanesulfonic acid;

(5-Chloro-2-{2-[4-(3,4-difluoro-benzyl)-2R,5S-dimethyl-piperazin-1-yl]-2-oxo-ethoxy}-pyridin-3-yl)-methanesulfonic acid;

(5-Chloro-2-{2-[4-(4-chloro-benzyl)-2R,5S-dimethyl-piperazin-1-yl]-2-oxo-ethoxy}-pyridin-3-yl)-methanesulfonic acid;

(5-Bromo-2-{2-[4-(4-chloro-benzyl)-2R,5S-dimethyl-piperazin-1-yl]-2-oxo-ethoxy}-pyridin-3-yl)-methanesulfonic acid;

(5-Chloro-2-{2-[4-(3,4-difluoro-benzyl)-2R-methyl-piperazin-1-yl]-2-oxo-ethoxy}-pyridin-3-yl)-methanesulfonic acid;

(5-Bromo-2-{2-[4-(3,4-difluoro-benzyl)-2R-methyl-piperazin-1-yl]-2-oxo-ethoxy}-pyridin-3-yl)-methanesulfonic acid;

(5-Chloro-2-{2-[4-(4-chloro-benzyl)-2R-methyl-piperazin-1-yl]-2-oxo-ethoxy}-pyridin-3-yl)-methanesulfonic acid;

(5-Bromo-2-{2-[4-(4-chloro-benzyl)-2R-methyl-piperazin-1-yl]-2-oxo-ethoxy}-pyridin-3-yl)-methanesulfonic acid;

2-(5-Chloro-2-{2-[4-(4-fluoro-benzyl)-2R,5S-dimethyl-piperazin-1-yl]-2-oxo-ethoxy}-pyridin-3-yl)-ethanesulfonic acid;

(5-Chloro-2-{2-[4-(3,4-difluoro-benzyl)-2R,5S-dimethyl-piperazin-1-yl]-2-oxo-ethoxy}-pyridin-3-yl)-ethanesulfonic acid;

(5-Bromo-2-{2-[4-(3,4-difluoro-benzyl)-2R,5S-dimethyl-piperazin-1-yl]-2-oxo-ethoxy}-pyridin-3-yl)-ethanesulfonic acid;

(5-Chloro-2-{2-[4-(4-chloro-benzyl)-2R,5S-dimethyl-piperazin-1-yl]-2-oxo-ethoxy}-pyridin-3-yl)-ethanesulfonic acid;

(5-Bromo-2-{2-[4-(4-chloro-benzyl)-2R,5S-dimethyl-piperazin-1-yl]-2-oxo-ethoxy}-pyridin-3-yl)-ethanesulfonic acid;

3-(5-Bromo-2-{2-[4-(3,4-difluoro-benzyl)-2R,5S-dimethyl-piperazin-1-yl]-2-oxo-ethoxy}-phenyl)-propane-1-sulfonic acid;

(5-Chloro-2-{2-[4-(4-fluoro-benzyl)-2R-methyl-piperazin-1-yl]-2-oxo-ethoxy}-pyridin-3-yl)-ethanesulfonic acid;

(5-Chloro-2-{2-[4-(3,4-difluoro-benzyl)-2R-methyl-piperazin-1-yl]-2-oxo-ethoxy}-pyridin-3-yl)-ethanesulfonic acid;

(5-Bromo-2-{2-[4-(3,4-difluoro-benzyl)-2R,5S-dimethyl-piperazin-1-yl]-2-oxo-ethoxy}-pyridin-3-yl)-methanesulfonic acid;

(5-Chloro-2-{2-[4-(4-chloro-benzyl)-2R-methyl-piperazin-1-yl]-2-oxo-ethoxy}-pyridin-3-yl)-ethanesulfonic acid;

3-(5-Chloro-2-{2-[4-(4-fluoro-benzyl)-2R,5S-dimethyl-piperazin-1-yl]-2-oxo-ethoxy}-pyridin-3-yl)-propane-1-sulfonic acid;

2-(5-Chloro-2-{2-[4-(4-fluoro-benzyl)-2R,5S-dimethyl-piperazin-1-yl]-2-oxo-ethoxy}-phenyl)-propane-2-sulfonic acid;

2-(5-Bromo-2-{2-[4-(4-fluoro-benzyl)-2R,5S-dimethyl-piperazin-1-yl]-2-oxo-ethoxy}-phenyl)-propane-2-sulfonic acid;

2-(5-Chloro-2-{2-[4-(4-fluoro-benzyl)-2R,5S-dimethyl-piperazin-1-yl]-2-oxo-ethoxy}-phenyl)-2-methyl-propane-1-sulfonic acid;

2-(5-Bromo-2-{2-[4-(4-fluoro-benzyl)-2R,5S-dimethyl-piperazin-1-yl]-2-oxo-ethoxy}-phenyl)-2-methyl-propane-1-sulfonic acid;

1-(5-Chloro-2-{2-[4-(4-fluoro-benzyl)-2R,5S-dimethyl-piperazin-1-yl]-2-oxo-ethoxy}-phenyl)-2-methyl-propane-2-sulfonic acid;

(2-{2-[4-(4-Fluoro-benzyl)-2R,5S-dimethyl-piperazin-1-yl]-2-oxo-ethoxy}-5-trifluoromethyl-phenyl)-methanesulfonic acid;

(2-{2-[4-(4-Fluoro-benzyl)-2R,5S-dimethyl-piperazin-1-yl]-2-oxo-ethoxy}-5-methyl-phenyl)-methanesulfonic acid;

(5-Chloro-2-{2-[2R-ethyl-4-(4-fluoro-benzyl)-5S-methyl-piperazin-1-yl]-2-oxo-ethoxy}-phenyl)-methanesulfonic acid;

(5-Bromo-2-{2-[2R-ethyl-4-(4-fluoro-benzyl)-5S-methyl-piperazin-1-yl]-2-oxo-ethoxy}-phenyl)-methanesulfonic acid;

(5-Chloro-2-{2-[2R-ethyl-4-(4-fluoro-benzyl)-5S-methyl-piperazin-1-yl]-2-oxo-ethoxy}-phenyl)-ethanesulfonic acid;

(5-Chloro-2-{2-[2R-ethyl-4-(4-fluoro-benzyl)-piperazin-1-yl]-2-oxo-ethoxy}-phenyl)-methanesulfonic acid;

(5-Bromo-2-{2-[2R-ethyl-4-(4-fluoro-benzyl)-piperazin-1-yl]-2-oxo-ethoxy}-phenyl)-methanesulfonic acid;

(5-Chloro-2-{2-[2R-ethyl-4-(4-fluoro-benzyl)-piperazin-1-yl]-2-oxo-ethoxy}-phenyl)-ethanesulfonic acid;

(5-Bromo-2-{2-[2R-ethyl-4-(4-fluoro-benzyl)-piperazin-1-yl]-2-oxo-ethoxy}-phenyl)-ethanesulfonic acid; and 1-(5-Bromo-2-{2-[4-(4-fluoro-benzyl)-2R,5S-dimethyl-piperazin-1-yl]-2-oxo-ethoxy}-phenyl)-2-methyl-propane-2-sulfonic acid.

45. A pharmaceutical composition for treating or preventing a disorder or condition selected from autoimmune diseases, lupus, acute and chronic inflammatory conditions, allergic conditions, infection associated with inflammation, viral, chronic bronchitis, xeno-transplantation, transplantation tissue rejection, atherosclerosis, restenosis, HIV infectivity, and granulomatous in a mammal, comprising an amount of a compound according to claim 26, or a pharmaceutically acceptable salt thereof, that is effective in treating or preventing such disorder or condition and a pharmaceutically acceptable carrier.

46. A pharmaceutical composition for treating or preventing a disorder or condition that can be treated or prevented by inhibiting MIP-1α and/or RANTES binding to the receptor CCR1 in a mammal, comprising an amount of a compound according to claim 26, or a pharmaceutically acceptable salt thereof, effective in treating or preventing such disorder or condition and a pharmaceutically acceptable carrier.

47. A method for treating or preventing a disorder or condition selected from autoimmune diseases, lupus, acute and chronic inflammatory conditions, allergic conditions, infection associated with inflammation, viral, chronic bronchitis, xeno-transplantation, transplantation tissue rejection, atherosclerosis, restenosis, HIV infectivity, and granulomatous in a mammal, comprising administering to a mammal an amount of a compound according to claim 26, or a pharmaceutically acceptable salt thereof, that is effective in treating or preventing such disorder or condition.

48. A method for treating or preventing a disorder or condition that can be treated or prevented by antagonizing the CCR1 receptor in a mammal, comprising administering to a mammal an amount of a compound according to claim 26, or a pharmaceutically acceptable salt thereof, that is effective in treating or preventing such disorder or condition.

49. A pharmaceutical composition for treating or preventing a disorder or condition that can be treated or prevented by antagonizing the CCR1 receptor in a mammal selected from autoimmune diseases, lupus, acute and chronic inflammatory conditions, allergic conditions, infection associated with inflammation, viral, chronic bronchitis, xeno-transplantation, transplantation tissue rejection, atherosclerosis, restenosis, HIV infectivity, and granulomatous in a mammal, comprising a CCR1 receptor antagonizing effective amount of a compound according to claim 26, or a pharmaceutically acceptable salt thereof, and a pharmaceutically acceptable carrier.

50. A pharmaceutical composition for treating or preventing a disorder or condition that can be treated or prevented by antagonizing the CCR1 receptor in a mammal, comprising a CCR1 receptor antagonizing effective amount of a compound according to claim 26, or a pharmaceutically acceptable salt thereof, and a pharmaceutically acceptable carrier.

51. A compound of (5-Chloro-2-{2-[4-(4-fluoro-benzyl)-2R,5S-dimethyl-piperazin-1-yl]-2-oxo-ethoxy}-phenyl)-methanesulfonic acid, or a pharmaceutically acceptable salt thereof.

52. A compound according to claims 19, 44, or 45, wherein the compound is a pharmaceutically acceptable salt of potassium or calcium.

53. A compound according to claims 19, 44, or 45, wherein the compound is a pharmaceutically acceptable salt of arginine or ethylene diamine.

* * * * *